(12) United States Patent
Kwon

(10) Patent No.: US 10,850,083 B2
(45) Date of Patent: Dec. 1, 2020

(54) METHOD FOR MANUFACTURING MICRONEEDLE BY USING BIOCOMPATIBLE POLYMER

(71) Applicant: Jieun Kwon, Seongnam (KR)

(72) Inventor: Jieun Kwon, Seongnam (KR)

( * ) Notice: Subject to any disclaimer, the term of this patent is extended or adjusted under 35 U.S.C. 154(b) by 274 days.

(21) Appl. No.: 16/077,020

(22) PCT Filed: Aug. 23, 2016

(86) PCT No.: PCT/KR2016/009330
§ 371 (c)(1),
(2) Date: Aug. 9, 2018

(87) PCT Pub. No.: WO2017/138682
PCT Pub. Date: Aug. 17, 2017

(65) Prior Publication Data
US 2019/0030309 A1 Jan. 31, 2019

(30) Foreign Application Priority Data
Feb. 11, 2016 (KR) .................. 10-2016-0015785

(51) Int. Cl.
*B29C 45/16* (2006.01)
*A61M 37/00* (2006.01)
(Continued)

(52) U.S. Cl.
CPC ....... *A61M 37/0015* (2013.01); *A61K 9/0021* (2013.01); *A61M 37/00* (2013.01);
(Continued)

(58) Field of Classification Search
None
See application file for complete search history.

(56) References Cited

U.S. PATENT DOCUMENTS

| 8,088,321 | B2* | 1/2012 | Ferguson | A61M 37/0015 264/328.7 |
| 2008/0088066 | A1* | 4/2008 | Ferguson | A61M 37/0015 264/443 |

(Continued)

FOREIGN PATENT DOCUMENTS

| KR | 1020100129958 A | 12/2010 |
| KR | 1020140051648 A | 5/2014 |

(Continued)

OTHER PUBLICATIONS

International Search Report for PCT/KR2016/009330 dated Nov. 1, 2016.

*Primary Examiner* — Edmund H Lee

(57) ABSTRACT

A method of manufacturing a biocompatible polymer-based microneedle, the method comprising: (a) a primary filling step of covering, by stoppers, upper sides of multiple holes, which are formed to be spaced apart from one another, penetrate a mold, and each have a conical shape, and injecting a biocompatible polymer solution containing an appropriate amount of active ingredient by using filling needles; (b) a secondary filling step of injecting a biocompatible polymer solution containing an excipient by using the filling needles; (c) a step of solidifying the biocompatible polymer solution; and (d) a step of attaching a pad to an upper portion of the mold and then detaching the pad from the mold. The microneedle manufactured by the present invention may solve problems of degeneration of medicine, insufficient hardness, and a loss of medicine caused by a complicated process and a long manufacturing time.

15 Claims, 16 Drawing Sheets

(51) Int. Cl.
*B29C 39/02* (2006.01)
*A61K 9/00* (2006.01)
*C08B 37/08* (2006.01)
*B29C 39/42* (2006.01)
*C08L 5/08* (2006.01)
*B29L 31/00* (2006.01)

(52) U.S. Cl.
CPC .............. *B29C 39/02* (2013.01); *B29C 39/42* (2013.01); *B29C 45/16* (2013.01); *B29C 45/1635* (2013.01); *C08B 37/0072* (2013.01); *C08L 5/08* (2013.01); *A61M 2037/0053* (2013.01); *A61M 2207/00* (2013.01); *B29K 2005/00* (2013.01); *B29L 2031/756* (2013.01); *B29L 2031/7544* (2013.01); *C08L 2201/06* (2013.01); *C08L 2203/02* (2013.01)

(56) References Cited

U.S. PATENT DOCUMENTS

| | | | |
|---|---|---|---|
| 2009/0326415 A1* | 12/2009 | Lim | A61B 5/150984 600/573 |
| 2013/0144217 A1* | 6/2013 | Ross | A61K 9/0021 604/173 |
| 2015/0141910 A1 | 5/2015 | Francis et al. | |
| 2017/0080196 A1* | 3/2017 | Lee | A61C 19/063 |
| 2017/0333691 A1* | 11/2017 | Kodama | B29C 45/2628 |
| 2020/0009767 A1* | 1/2020 | Li | A61M 37/0015 |

FOREIGN PATENT DOCUMENTS

| | | |
|---|---|---|
| KR | 1020140141360 A | 12/2014 |
| WO | 2007080427 A2 | 7/2007 |
| WO | 2015010599 A1 | 1/2015 |

\* cited by examiner

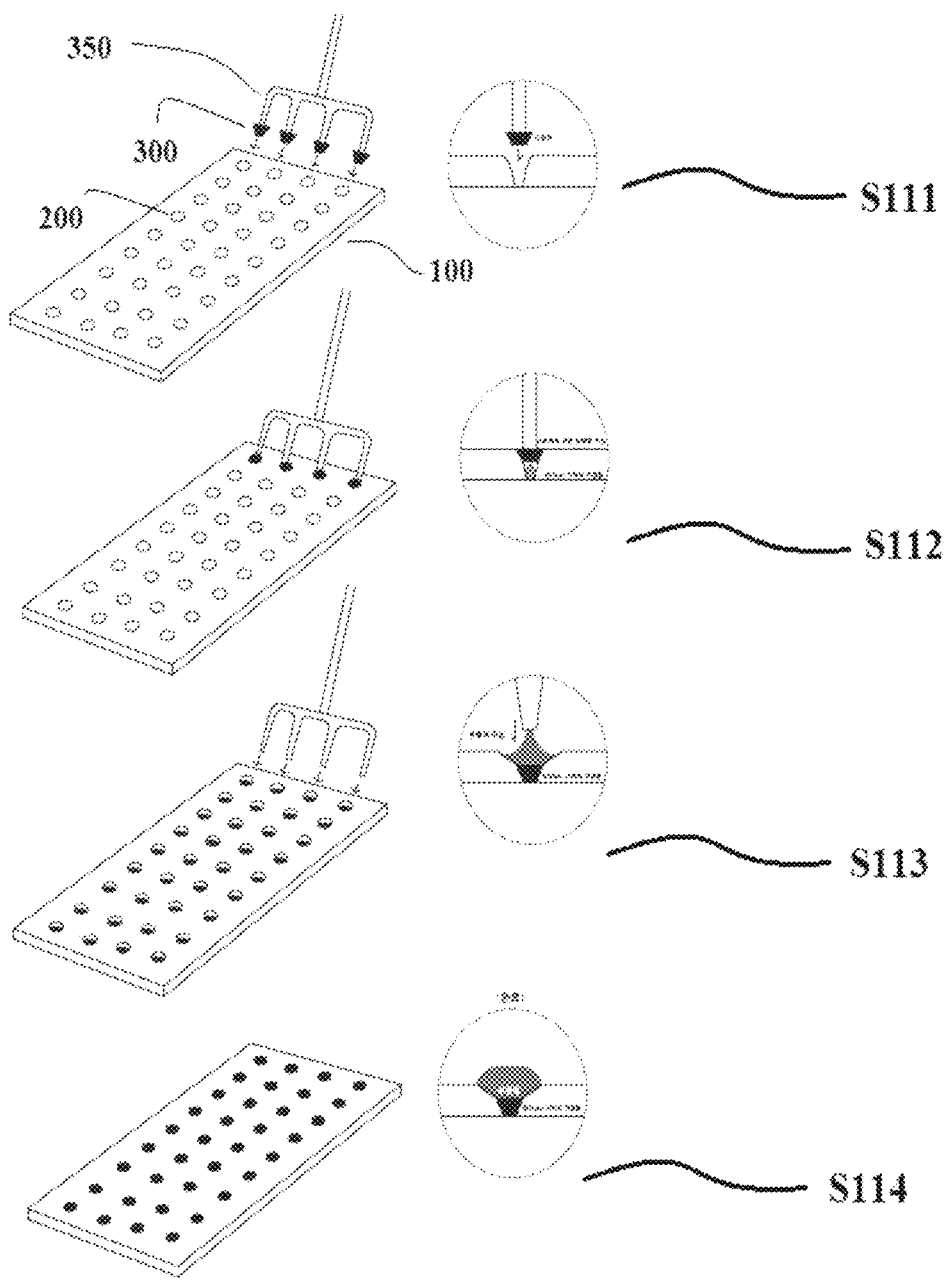
[Fig. 1]

[Fig. 2]
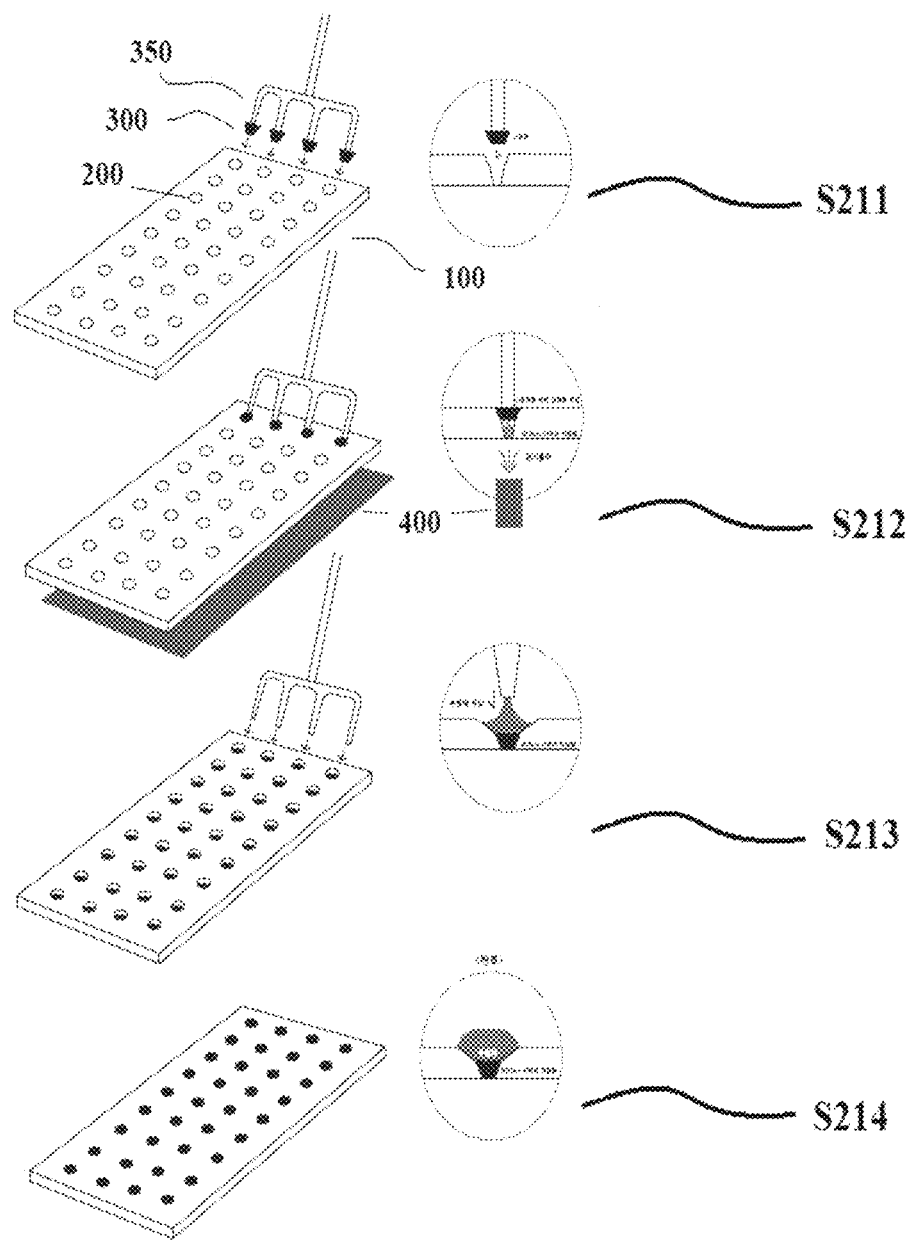

[Fig. 3]
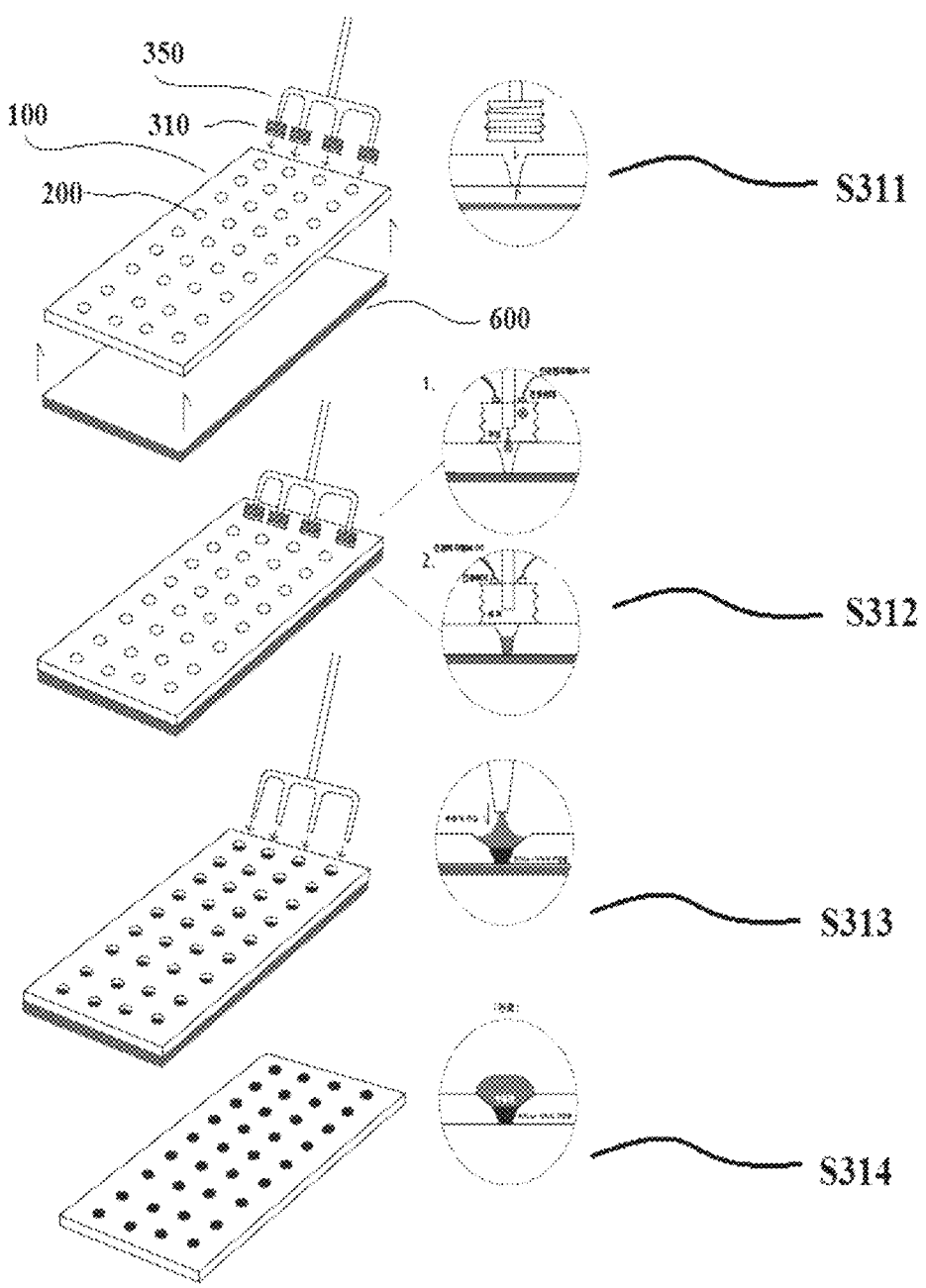

[Fig. 4]
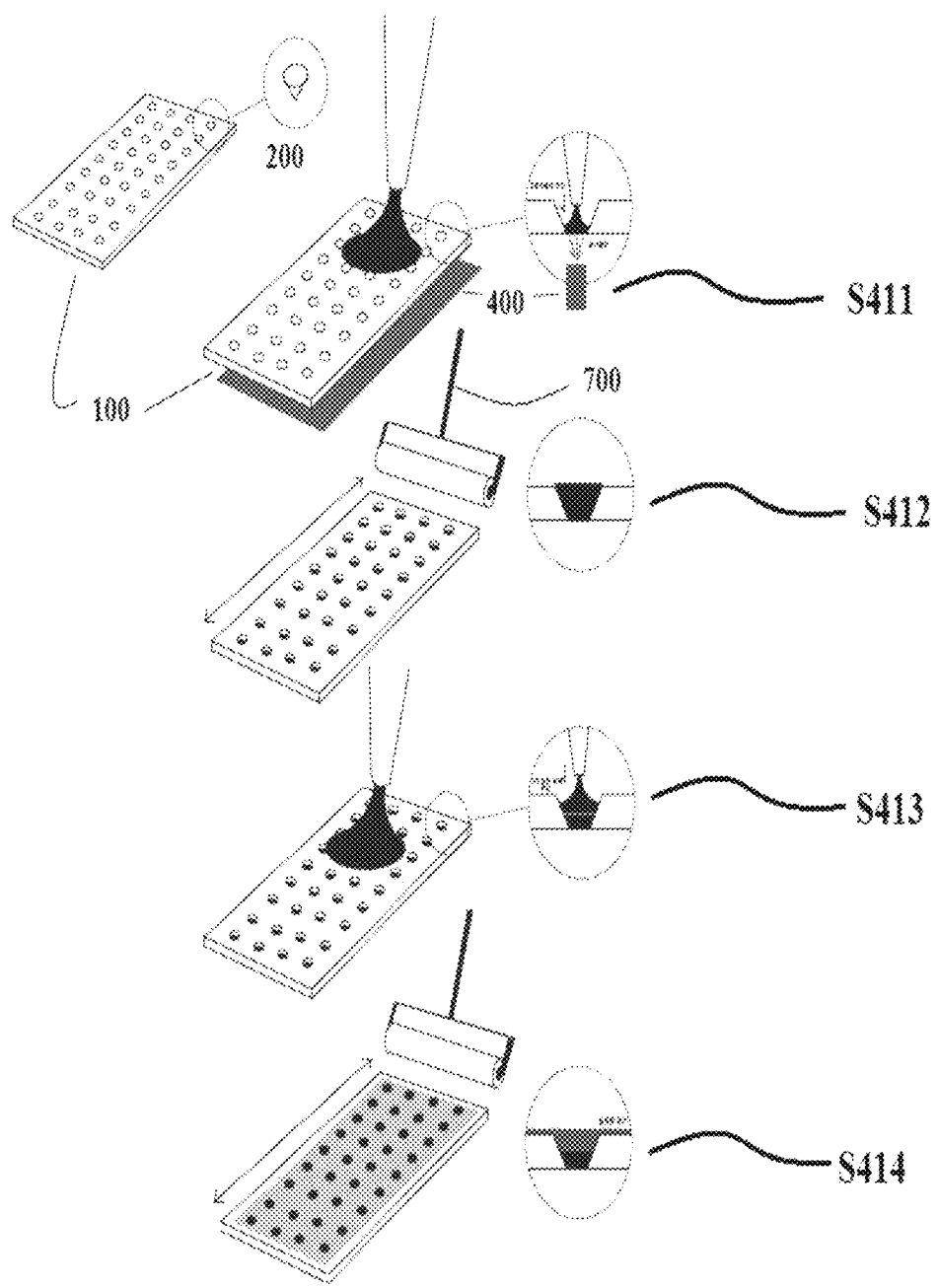

[Fig. 5]
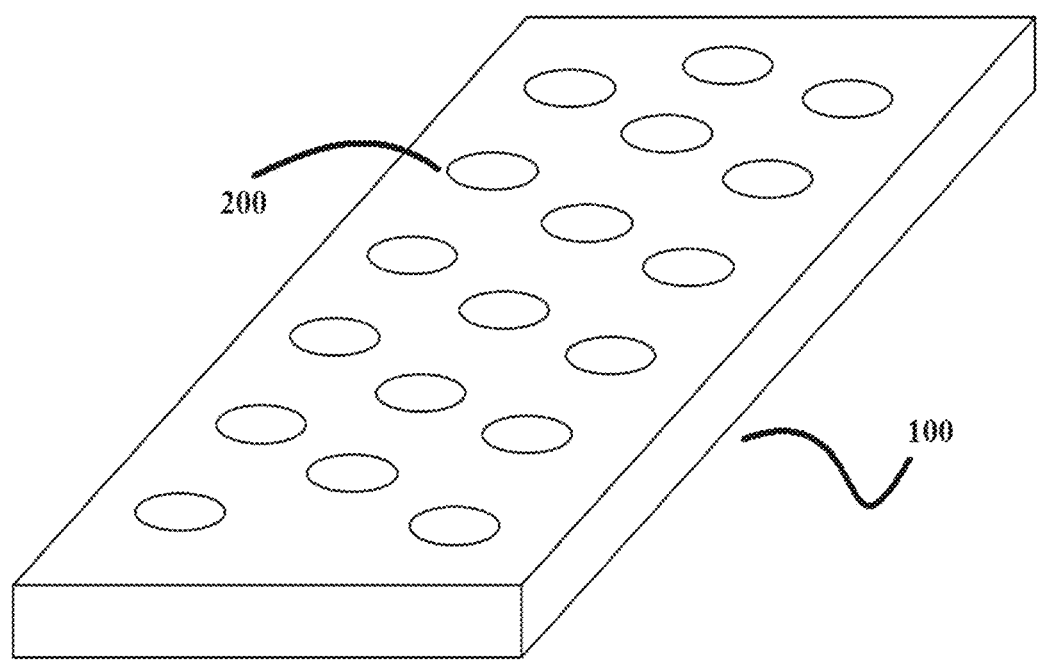

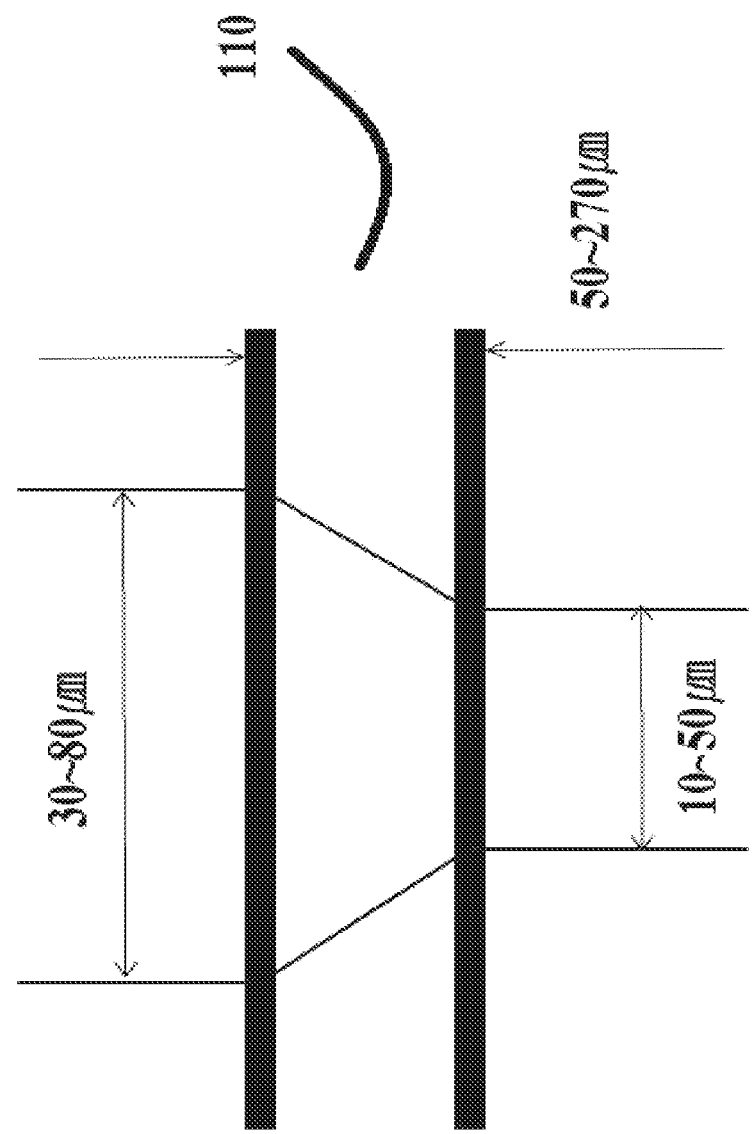
[FIG. 6a]

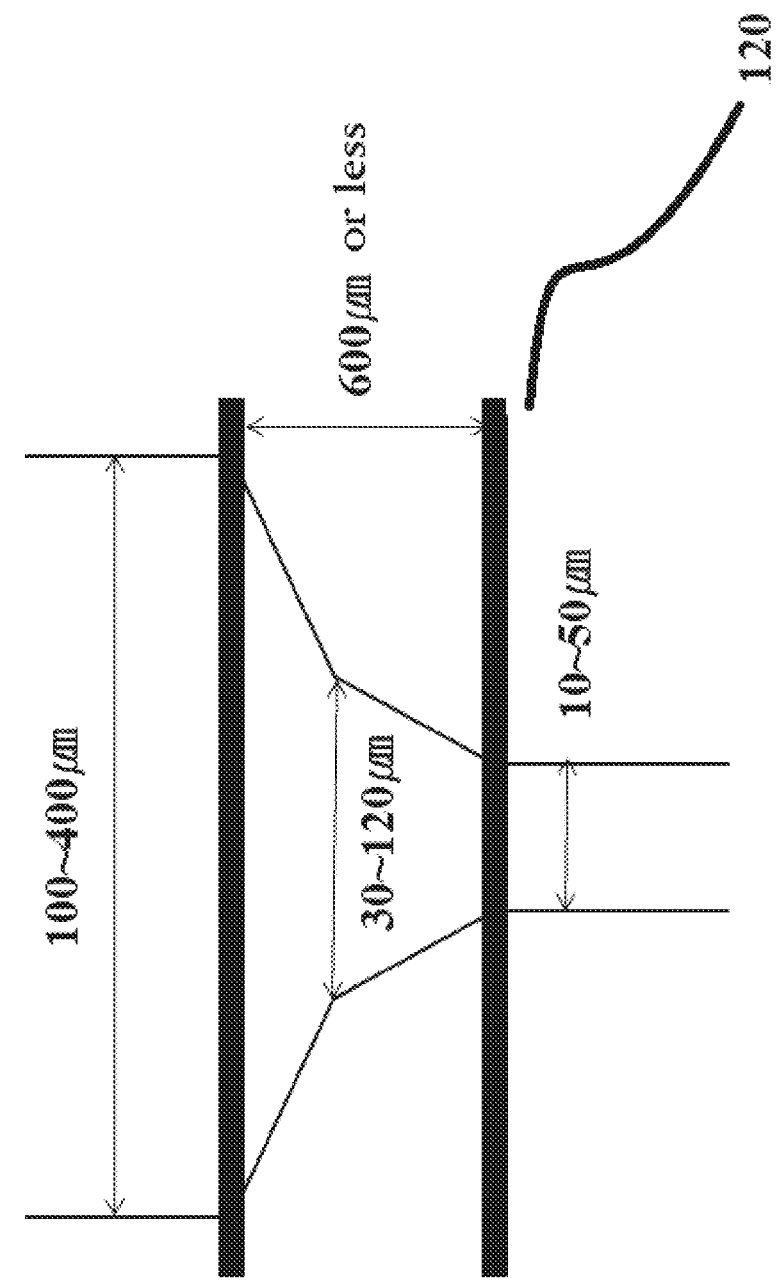
[Fig. 6b]

[Fig. 7]
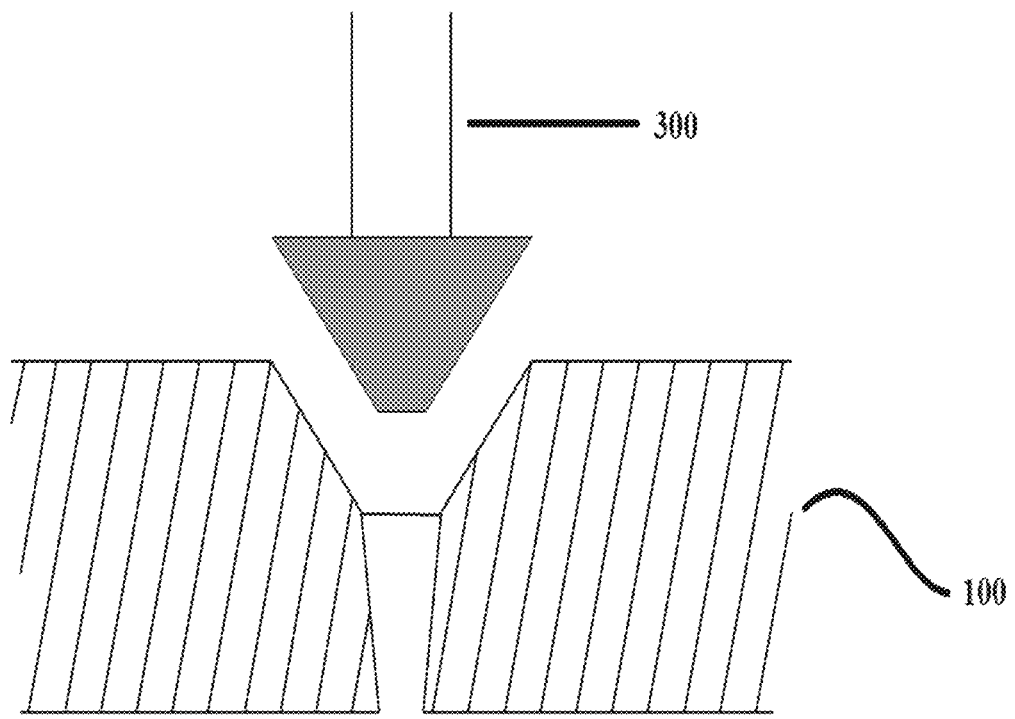

[Fig. 8]
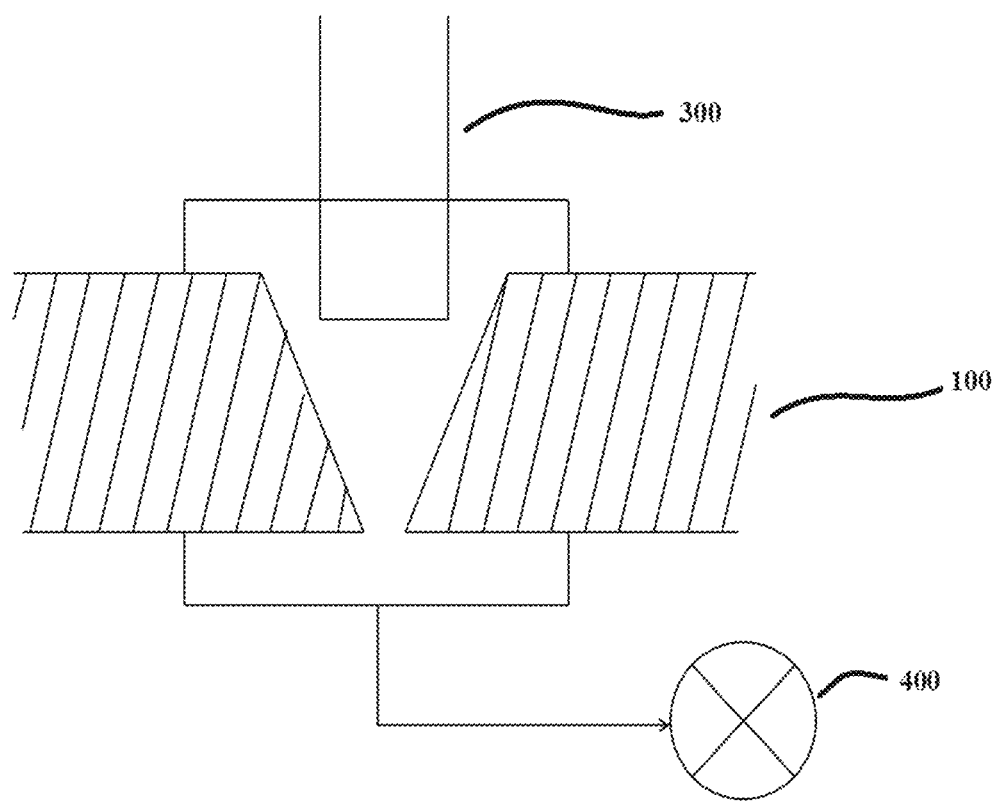

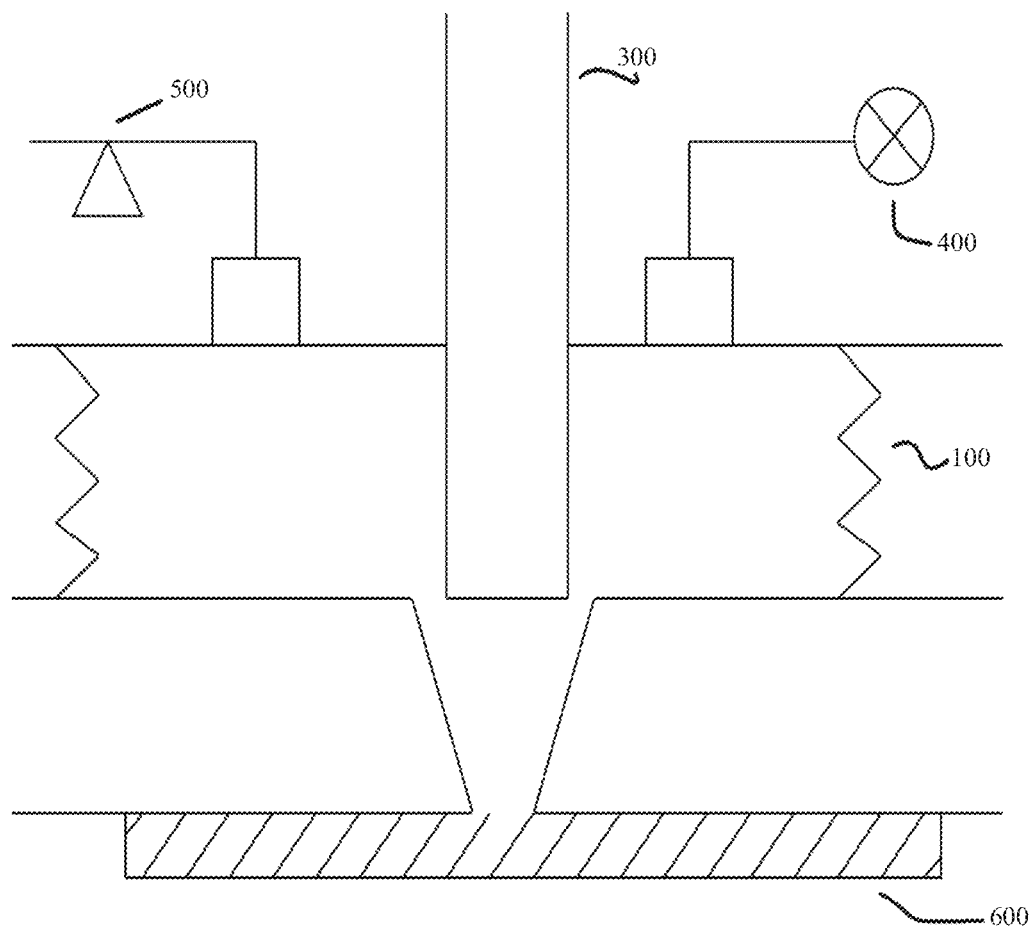
[Fig. 9]

[Fig. 10]
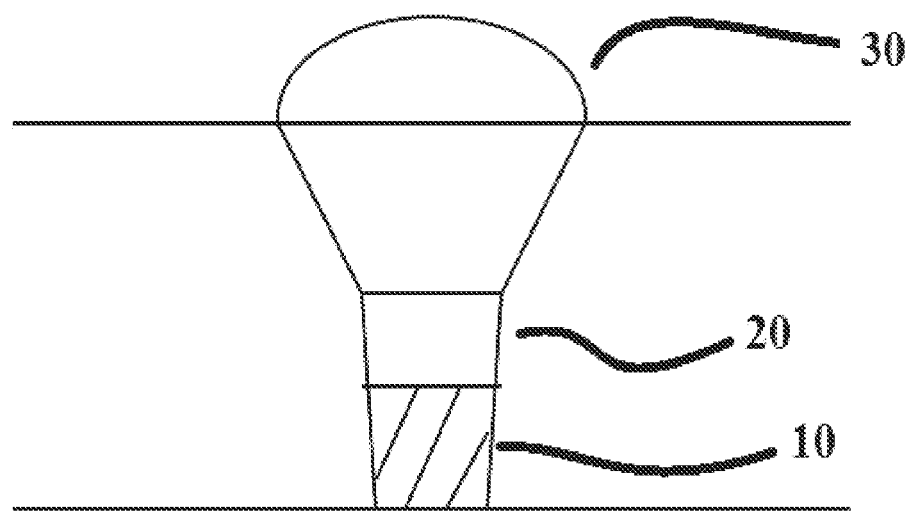

[Fig. 11]
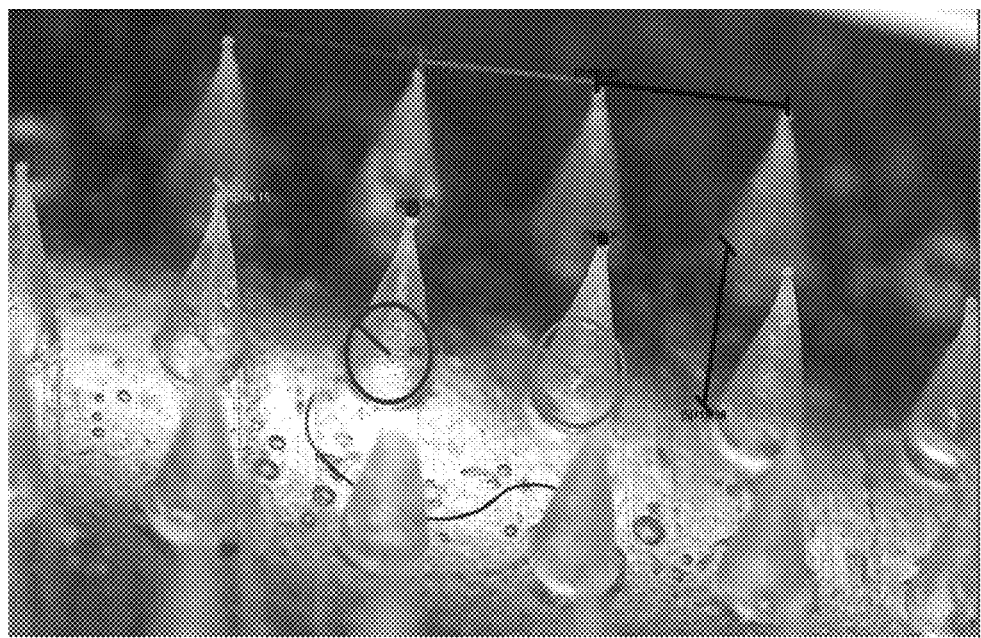

[Fig. 12a]
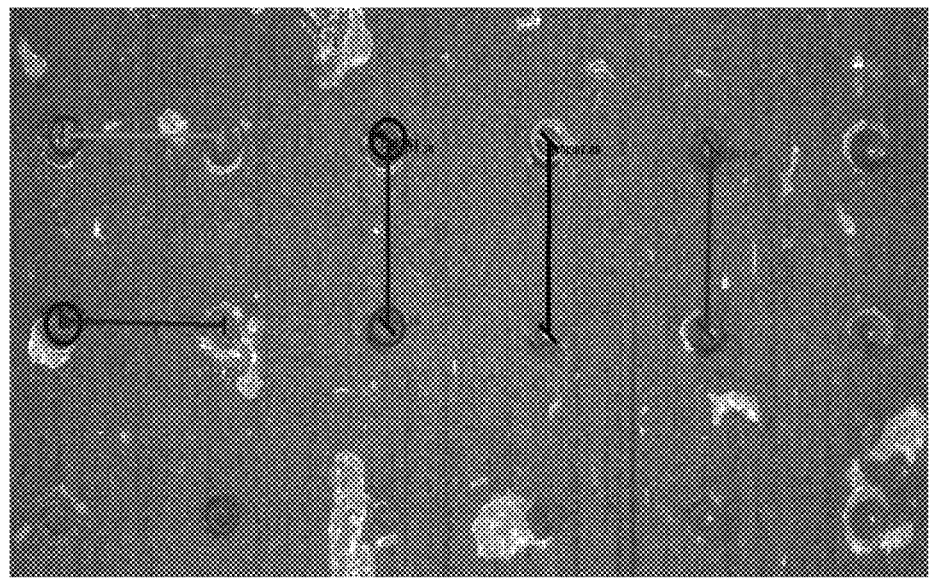
[Fig. 12b]
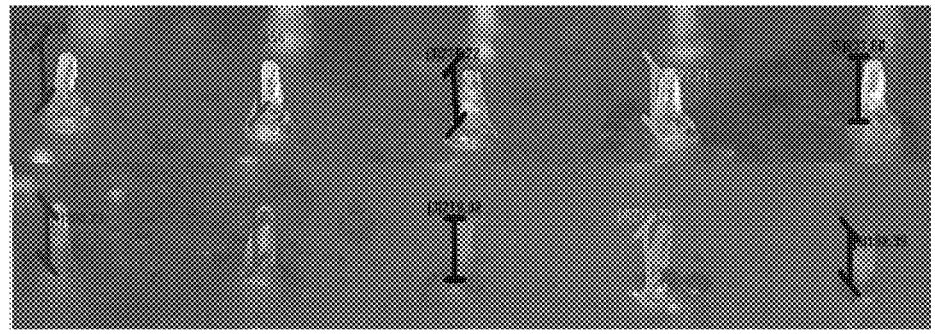
[Fig. 12c]
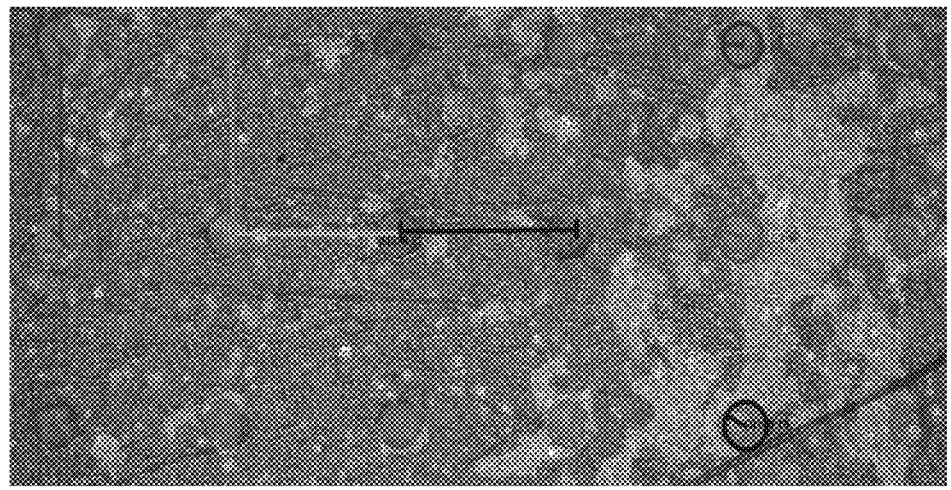

[Fig. 12d]
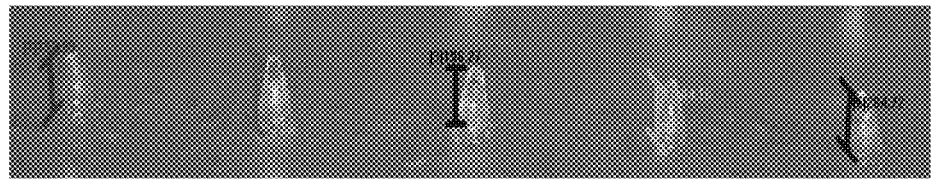
[Fig. 13a]
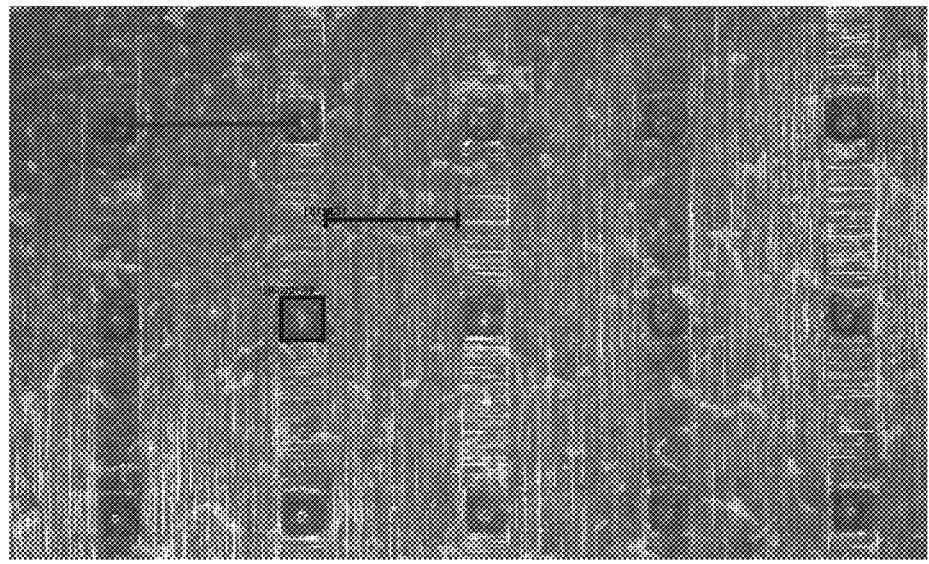
[Fig. 13b]
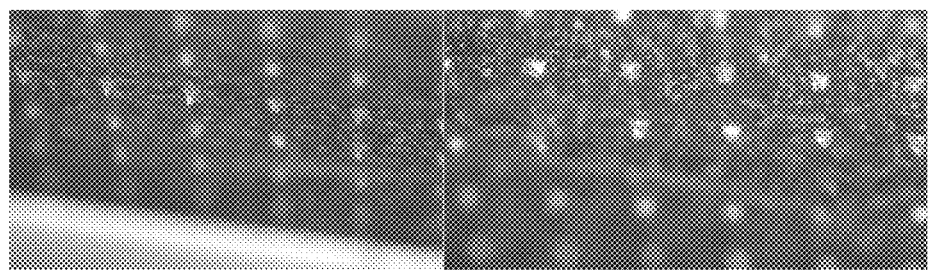
[Fig. 14]
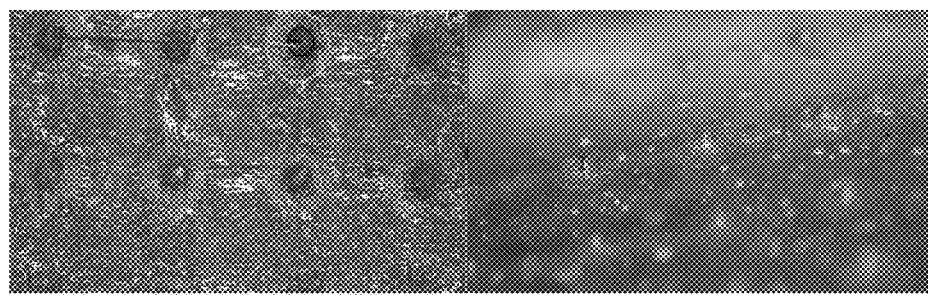

[Fig. 15a]
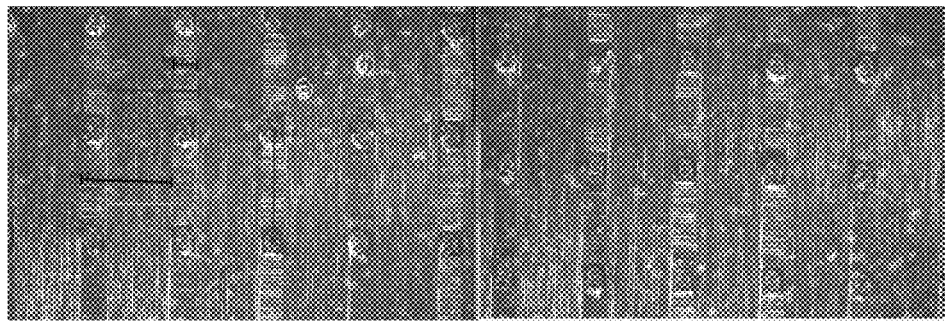
[Fig. 15b]
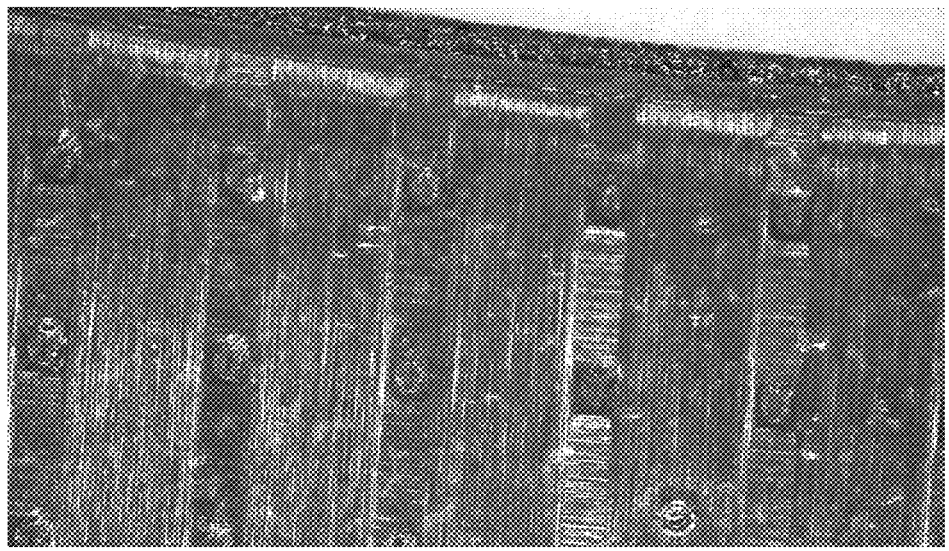
[Fig. 15c]
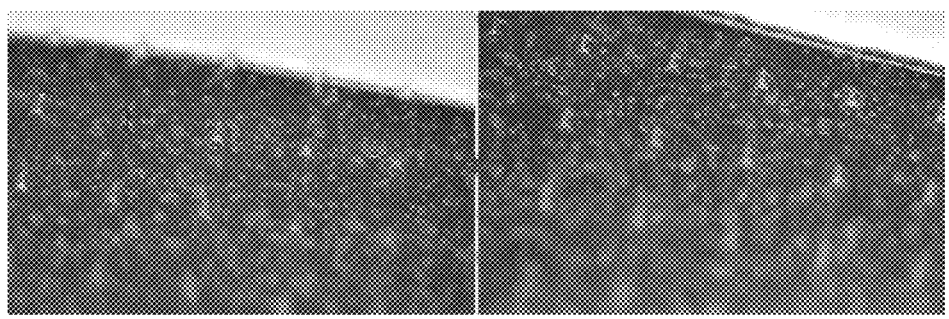

[Fig. 15d]
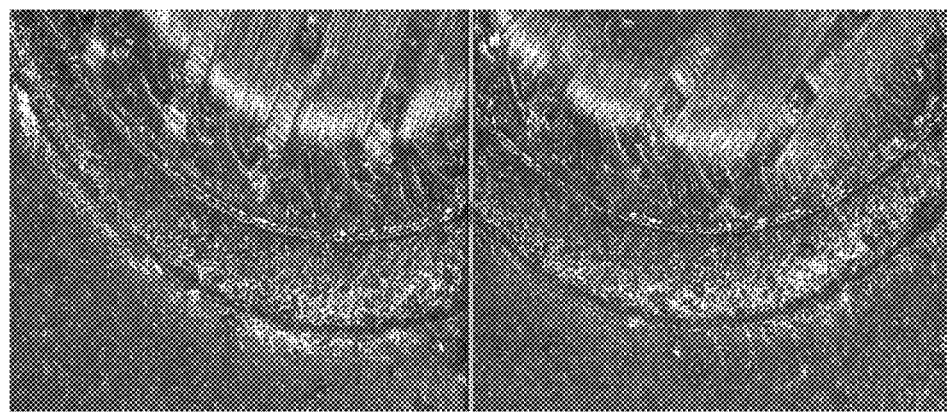
[Fig. 15e]
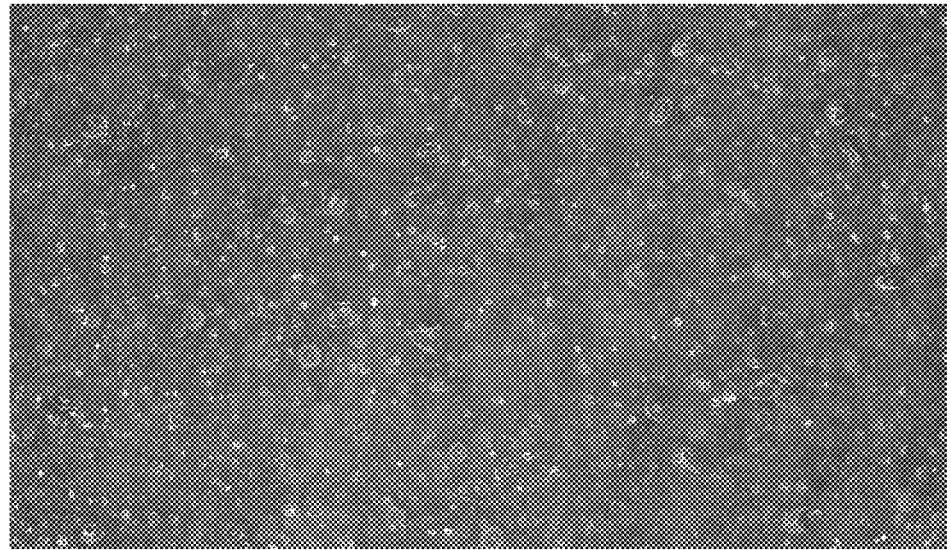

US 10,850,083 B2

METHOD FOR MANUFACTURING MICRONEEDLE BY USING BIOCOMPATIBLE POLYMER

TECHNICAL FIELD

The present invention relates to a microneedle manufacturing method using a biocompatible polymer, and more particularly, to a method of simply and economically manufacturing a microneedle that may realize sufficient hardness and painlessness without causing a loss and degeneration of medicine because the microneedle is manufactured by filling holes, which are formed to be spaced apart from one another in a mold, with a biocompatible polymer solution such as a hyaluronic acid solution by using a stopper capable of applying pressure to the mold, and a fine filling needle and/or a vacuum pump, and then solidifying the biocompatible polymer solution.

BACKGROUND ART

A method of injecting medicine in a liquid phase by using a subcutaneous injection needle is widely used as a method of effectively delivering medicine to be applied to a human body. However, there are problems in that a subcutaneous injection needle or an intramuscular injection needle having a diameter of 100 μm or more irritates multiple pain spots existing on skin, thus causing a patient pain which may lead to a phobia to needles, local damage to the skin, and bleeding, a high degree of skill is required to use the needle, and disease infection occurs at an injection site.

To solve the aforementioned problems of the subcutaneous injection needle, researches on a method of transdermally delivering medicine by using a microneedle device just having a diameter and a height of 10 to 100 μm to be applied to a human body are being actively conducted. The microneedle device forms, at one time, multiple channels, which penetrate a skin portion, by using microneedles that penetrate a horny layer of the skin which is a main barrier layer acting against the transdermal delivery of the medicine. A sufficient amount of medicine may reach an epidermal layer or a dermal layer through the channels, and thereafter, the medicine is absorbed through blood vessels and lymph nodes and then delivered into a circulatory system in the human body. In addition, the microneedle may be used for a cosmetic purpose. For example, a bioactive material is applied onto the skin or the microneedles, microchannels are formed in the skin by the microneedle, and then the bioactive material is transdermally delivered. The method of transdermally delivering an effective material by using the microneedles is very useful, but a microneedle device of a patch type, which is made by simplifying a microneedle device having a complicated structure in the related art, is used more usefully.

A diameter of an upper end of the microneedle is very important in view of having high sharpness since the feature of the microneedle is to penetrate the skin without pain, and the microneedle needs to have sufficient physical hardness since the microneedle needs to penetrate a horny layer of 10 to 20 μm. In addition, an appropriate length of the microneedle, which allows the microneedle to reach capillaries to improve efficiency in delivering medicine, is one of the important elements.

Various types of microneedles including in-plane type microneedles or out-of-plane type microneedles have been developed, an etching method and a photolithographic method are used as a method of manufacturing the microneedles, and a combination of the etching method and the photolithographic method may be used.

U.S. Patent Application Publication No. 2002-138049 discloses a method of manufacturing an out-of-plane type solid microneedle by using an etching method, and this etching method may manufacture a solid silicone microneedle having a diameter of 50 to 100 μm and a length of 500 μm, but it is impossible to penetrate skin without pain, and it is difficult to deliver medicine and a cosmetic ingredient to a target site.

A method of manufacturing a biocompatible solid microneedle by mounting a material manufactured in the form of a capsule by using the photolithographic method is publicly known, and this method has an advantage in freely mounting medicine that may be manufactured in the form of a capsule, but this method has a problem that hardness of the microneedle deteriorates as the amount of mounted medicine is increased, such that this method cannot be applied for medicine required to be injected in a large amount (Jung-Hwan P., et al., Pharmaceutical Research, Vol. 23, No. 5, May 2006).

Japanese Patent Application Laid-Open No. 2005-154321 discloses a method of manufacturing an absorptive microneedle by applying a composition made by mixing maltose and medicine to a mold and solidifying the composition. According to this Japanese Patent Application, the absorptive microneedle is manufactured for the purpose of transdermally absorbing the medicine, but there are problems in that the absorptive microneedle causes pain when penetrating the skin, and because of a technical limitation in manufacturing a mold, it is impossible to manufacture a microneedle which has a diameter at an upper end appropriate to painlessness and a length at a level required for an effective delivery of medicine, that is, a length of 1 mm or more. In addition, the method of manufacturing the microneedle by using the mold requires additional processes that need to manufacture a new mold and a new frame through complicated processes to adjust the diameter and the length of the microneedle, and there are problems in that the process of manufacturing the microneedle by inserting a material into the mold is complicated and requires a large amount of time.

A biodegradable microneedle, which is manufactured in a polydimethylsiloxane (PDMS) mold by using a material made by mixing polyvinylpyrrolidone (PVP) and methacrylic acid (MAA), is publicly known (Sean P Sullivan et al., Advanced Materials 2008, 1). In addition, a microneedle is sometimes manufactured by inserting carboxymethylcellulose into a mold having a pyramidal structure (Jeong Woo Lee et al., Biomaterials 2007, 1). However, there is a limitation in that the method of manufacturing the microneedle by using the mold requires additional processes that need to manufacture a new mold and a new frame through complicated processes to adjust the diameter and the length of the microneedle, and there are problems in that the process of manufacturing the microneedle by inserting a material into the mold is complicated and requires a large amount of time.

In addition, U.S. Patent Application Publication No. 20080157421 A1 discloses an apparatus and a method of manufacturing a skin needle by using a pin structure. The method uses a method of pulling a heated or viscous material on a base of a substrate by using a pin by using tensile force. Since this method uses the method of pulling a material, which is melted by heat or has viscosity, by using the pin structure, this method cannot overcome limitations in that a process of newly manufacturing the pin structure in accordance with a desired pattern is required, which causes an increase in production costs, and it is difficult to mount various biological medicines sensitive to heat because of the heating process.

In addition, Korean Patent No. 10-1254240discloses a method of manufacturing a microneedle by forming a bottom layer by applying and drying a viscous material, spotting a viscous composition, bringing a substrate into contact with the viscous composition, and extending and solidifying the composition. This method is performed by dripping an appropriate amount of hyaluronic acid onto a plate and then extending the hyaluronic acid by using another plate or tool, but it is difficult to appropriately adjust a thickness or a length of the hyaluronic acid when extending the hyaluronic acid, viscosity of the hyaluronic acid is not constant because of the nature of the hyaluronic acid, and the hyaluronic acid is greatly affected by an environment, particularly, an exposure temperature and humidity. In addition, it is difficult to expect to obtain a needle having a constant shape and a constant size when cutting the hyaluronic acid while solidifying the hyaluronic acid by using blowing or a temperature after extending the temperature, and there is difficulty in managing process efficiency.

In addition, Korean Patent No. 10-0943157 discloses a mold for manufacturing a fine needle array having fine needle patterns through processes of embossing and dicing fine needle patterns by using a semiconductor etching process. According to the mold for manufacturing an array according to the method, it is difficult to expect to obtain a very fine needle because of the nature of the processing. In particular, the needle has a good external appearance because the mold is used, but because of the limitation of the mold, particularly, a limitation in precision after assembling the needle, there are problems in that it is mechanically difficult to manufacture a needle having a size of 10 to 50 µm, and thus it is difficult to overcome the phobia to needles even though the advantage of this product is to overcome the phobia to needles. In addition, there are many problems when ensuring both stability and effectiveness to apply medicines to the needle. For example, the needle needs to be used aseptically even to perform subcutaneous injection, but because the extension or array type needle often interferes with a person, it is very difficult to implement an aseptic product in the current situation.

The needle needs to supply a sufficient amount of main ingredient having effectiveness only to a necessary site, but there is a limitation in that both of Korean Patent No. 10-1254240 and Korean Patent No. 10-0943157 use and apply the same filling solution or cannot do so.

Accordingly, the present inventors have made an effort to solve the aforementioned problems and completed the present invention after finding out that in a case in which holes formed to be spaced apart from one another in a mold are filled with a biocompatible polymer solution such as a hyaluronic acid solution by using a pressing stopper, a fine filling needle and/or a vacuum pump, it is possible to solve problems of degeneration of medicine, insufficient hardness, and a loss of medicine caused by a complicated process and a long manufacturing time of a solid microneedle manufacturing method in the related art, no pain is incurred when penetrating the skin, the microneedle has a diameter, hardness, and a length that may penetrate into the skin when the microneedle is used for a medicine purpose or sufficiently stimulate the skin when the microneedle is used for a cosmetic purpose, and the microneedle, which has a perfect shape and is based on a biocompatible polymer, may be simply manufactured.

DISCLOSURE

Technical Problem

An object of the present invention is to provide a method of manufacturing a microneedle which is easily inserted into skin, may be penetrate deep into the skin, may accurately deliver a substantially necessary main ingredient to a target site in the skin without a degeneration or loss of medicine, may be manufactured aseptically, and has a constant shape and a constant size.

Another object of the present invention is to provide a method of manufacturing a biocompatible polymer-based microneedle which enables a patient to give himself/herself a treatment (injection) at the right time regardless of time and place, and may minimize a shock caused by a rapid injection.

Still another object of the present invention is to provide a method of manufacturing a biocompatible polymer-based microneedle which is more simply manufactured in a short time in comparison with a method of manufacturing a microneedle in the related art.

Technical Solution

To achieve the aforementioned objects, the present invention provides a method of manufacturing a biocompatible polymer-based microneedle, the method including: (a) a primary filling step of covering, by stoppers, upper sides of multiple holes 200 of the mold 100, which are formed to be spaced apart from one another, penetrate a mold 100, and each have a conical shape, and injecting a biocompatible polymer solution containing an appropriate amount of active ingredient by using filling needles 350; (b) a secondary filling step of injecting a biocompatible polymer solution containing an excipient by using the filling needles 350; (c) a step of solidifying the biocompatible polymer solution; and (d) a step of attaching a pad to an upper portion of the mold 100 and then detaching the pad from the mold 100.

The present invention also provides a method of manufacturing a biocompatible polymer-based microneedle, the method including: (a) a primary filling step of covering, by the stoppers, the upper sides of the multiple holes 200, which are formed to be spaced apart from one another, penetrate the mold 100, and each have a conical shape, forming a vacuum at the lower sides of the holes 200, and injecting the biocompatible polymer solution containing an appropriate amount of active ingredient by using the filling needles 350; (b) a secondary filling step of injecting the biocompatible polymer solution containing the excipient by using the filling needle 350; (c) a step of solidifying the biocompatible polymer solution; and (d) a step of attaching the pad to the upper portion of the mold 100 and detaching the pad from the mold 100.

The present invention also provides a method of manufacturing a biocompatible polymer-based microneedle, the method including: (a) a primary filling step of positioning a pad 600 at the lower side of the bottom of the mold 100 having the multiple holes 200, which are formed to be spaced apart from one another, penetrate the mold, and each have a conical shape to seal the lower side of the bottom of the mold, covering, by the vacuum stopper, the upper sides of the holes 200, dripping the biocompatible polymer solution containing an appropriate amount of active ingredient in the vacuum state, releasing the vacuum, and then filling the holes with the biocompatible polymer solution; (b) a secondary filling step of injecting the biocompatible polymer solution containing the excipient by using the filling needles 350; (c) a step of solidifying the biocompatible polymer solution; and (d) a step of attaching the pad 600 to the upper portion of the mold 100 and then detaching the pad from the mold 100.

The present invention also provides a method of manufacturing a biocompatible polymer-based microneedle, the method including: (a) a step of dripping and uniformly applying the biocompatible polymer solution containing an appropriate amount of active ingredient onto the mold 100 having the multiple holes 200 which are formed to be spaced apart from one another, penetrate the mold 100, and each have a conical shape, and injecting the biocompatible polymer solution by connecting the lower sides of the holes 200 of the mold 100 to the vacuum pump; (b) a step of repeating step (a) one to ten times; (c) a step of solidifying the biocompatible polymer solution; and (d) a step of attaching the pad to the upper portion of the mold 100 and then detaching the pad from the mold 100.

DESCRIPTION OF DRAWINGS

FIGS. 1 to 4 are flowcharts schematically illustrating a method of manufacturing a biocompatible polymer-based microneedle according to an exemplary embodiment of the present invention.

FIG. 5 is a perspective view of a mold used for the method of manufacturing the biocompatible polymer-based microneedle according to the exemplary embodiment of the present invention.

FIG. 6A is a cross-sectional view of a microneedle mold used for the method of manufacturing a biocompatible polymer-based microneedle for a cosmetic purpose according to the exemplary embodiment of the present invention.

FIG. 6B is a cross-sectional view of a microneedle mold used for the method of manufacturing the biocompatible polymer-based microneedle for a medicine purpose according to the exemplary embodiment of the present invention.

FIGS. 7 to 9 are views illustrating in cross-sectional views a process of manufacturing the biocompatible polymer-based microneedle according to the exemplary embodiments of the present invention.

FIG. 10 is a cross-sectional view of a biocompatible polymer-based microneedle patch manufactured according to the exemplary embodiment of the present invention.

FIG. 11 is a photomicrograph (magnification of ×60) of a cross-linked hyaluronic acid-based microneedle for a medicine purpose which is manufactured according to the exemplary embodiment of the present invention.

FIGS. 12A-12D are photomicrographs (magnification of ×60) obtained by capturing an elevational view (FIG. 12A) and a side view (FIG. 12B) of a low-concentration cross-linked hyaluronic acid-based microneedle manufactured according to the exemplary embodiment of the present invention, and photomicrographs (magnification of ×60) obtained by capturing an elevational view (FIG. 12C) and a side view (FIG. 12D) of a high-concentration cross-linked hyaluronic acid-based microneedle.

FIGS. 13A and 13B are photomicrographs (magnification of ×60) obtained by capturing an elevational view (FIG. 13A) and a side view (FIG. 13B) of a commercially available microneedle from Company A.

FIG. 14 is photomicrographs (magnification of ×60) obtained by capturing an elevational view (left) and a side view (right) of a commercially available microneedle from Company B.

FIGS. 15A-15E are photomicrographs obtained by capturing an elevational view (FIG. 15A), an elevational zoom-in view (FIG. 15B), a side view (FIG. 15C), an edge (FIG. 15D), and an attachment portion (FIG. 15E) of a commercially available microneedle from Company C.

DESCRIPTION OF MAIN REFERENCE NUMERALS OF DRAWINGS

100: mold
110: mold for cosmetic purpose
120: mold for medicine purpose
200: hole
300: stopper
310: vacuum stopper
350: filling needle
400: vacuum pump
500: vacuum releasing valve
600: pad
700: roller
10: pharmaceutically active ingredient
20: excipient ingredient
30: patch attachment portion

BEST MODE

Unless otherwise defined, all technical and scientific terms used in this specification have the same meaning as commonly understood by the person skilled in the art to which the present invention pertains. In general, the nomenclature used in the specification is well known and commonly used in the present technical field.

The present invention has been completed after finding out that in a case in which a biocompatible polymer-based microneedle is manufactured by filling holes 200 formed to be spaced apart from one another in a mold 100 with a biocompatible polymer solution such as a hyaluronic acid solution by using stoppers 300 and fine filling needles 350 and/or a vacuum pump 400 and solidifying the biocompatible polymer solution, an end of the needle is sharp at a level of 25 to 30%, the microneedle is easily inserted into skin when penetrating the skin such that the needle penetrates deep into the skin, the needle thinly shrinks by about 20% or more in comparison with a case in which a size of a needle is filled in accordance with a method of solidifying the biocompatible polymer solution in the mold 100, no pain is incurred because the needle is thinner than a microneedle in the related art such that feeling is less when the needle is inserted into the skin, and the biocompatible polymer-based microneedle capable of accurately administering medicine to a target site without causing a degeneration or loss of the medicine may be simply manufactured in a short time.

The term "microneedle" used in the present specification means a term including a needle portion and an underlying layer, and the term "needle" means a portion filled with an active ingredient and an excipient that fills an end of the needle.

A method of filling the mold with the biocompatible solution such as the hyaluronic acid according to the present invention will be described below.

(1) The stopper 300 made of various types of materials covers an upper side of the hole 200 of the mold 100 according to the present invention and presses the biocompatible solution to inject a predetermined amount of biocompatible solution, and whether all of the holes 200 are filled with the predetermined amount of injected biocompatible solution is checked by using a vision system.

(2) The stopper 300 covers the upper side of the hole 200 of the mold 100 according to the present invention and presses the biocompatible solution while a vacuum is simultaneously formed at a lower side of the hole 200 to inject a predetermined amount of biocompatible solution, and whether all of the holes 200 are filled with the predetermined amount of injected biocompatible solution is checked by using the vision system.

(3) A pad 600 such as a silicone pad or a rubber pad is positioned at a lower side of a bottom of the mold 100 according to the present invention to seal the lower side of the bottom of the mold 100, a vacuum is formed at the upper side of the hole 200 by using a vacuum stopper 310, a predetermined amount of biocompatible solution fills the hole 200 in a vacuum state, and when the vacuum is released after the biocompatible solution is completely injected into the hole 200, the hole 200 is filled with the biocompatible solution as air in the hole is removed. In this case, the pad 600 at the lower side is removed, and whether all of the holes 200 are filled with the amount of injected solution is checked by using the vision system.

The reason why the processes of the present invention are possible is that the polymeric solution does not continuously flow downward due to viscoelasticity of polymeric materials but remains at a position at which the polymeric solution fills the hole. A biocompatible polymer or a biocompatible polymer with a low degree of cross-linking may be used as the polymer, and particularly, hyaluronic acid or cross-linked hyaluronic acid with a low degree of cross-linking (3 to 5%) may be used.

Therefore, one aspect of the present invention relates to a method of manufacturing a biocompatible polymer-based microneedle, the method including: (a) a primary filling step of covering, by the stoppers, the upper sides of the multiple holes 200 of the mold 100, which are formed to be spaced apart from one another, penetrate the mold 100, and each have a conical shape, and injecting the biocompatible polymer solution containing an appropriate amount of active ingredient by using the filling needles 350; (b) a secondary filling step of injecting the biocompatible polymer solution containing an excipient by using the filling needles 350; (c) a step of solidifying the biocompatible polymer solution; and (d) a step of attaching a pad to an upper portion of the mold 100 and then detaching the pad from the mold 100.

As illustrated in FIG. 1, a first method according to the present invention sequentially fills the multiple holes 200 with an accurate amount of the completely prepared solution having the biocompatible polymer and the main ingredient by using the stoppers 300 and the fine filling needles 350 (S111 and S112). After the multiple holes 200 are completely filled, the multiple holes 200 are filled with the solution containing the biocompatible polymer secondarily or tertiarily (S113), and the reason is that this process serves to push the main ingredient of the raw liquid so that the ingredient is positioned at the end of the needle, and a protruding portion at the upper portion is a portion to be attached to the pad (tape) (S114). In some instances, the tertiary filling applies cosmetics onto the upper portion of the mold 100 to make a constant thickness once more, and then the mold 100 is moved to a chamber to solidify the solution. When the solidification is completed, the solidified material is separated from the mold 100 and attached onto the pad (tape). As illustrated in FIG. 7 in more detail, the stopper 300 made of silicone or rubber covers the hole 200 of the mold 100 according to the present invention and presses the solution to inject a predetermined amount of solution, and whether all of the holes 200 are filled with the amount of injected solution and whether the solution is appropriately solidified after the solution is solidified are checked by using the vision system. In this case, a temperature of the solution to be injected may be 10 to 65° C. The temperature may vary depending on the nature, viscosity, and elasticity of the product. However, in the case of a biological product, an appropriate temperature may be applied sufficiently considering sensitivity to heat.

In the manufacturing method, the vacuum may be applied by connecting the lower side of the hole 200 to the vacuum pump 400 when step (a) is performed.

Therefore, another aspect of the present invention relates to a method of manufacturing a biocompatible polymer-based microneedle, the method including: (a) a primary filling step of covering, by the stoppers, the upper sides of the multiple holes 200, which are formed to be spaced apart from one another, penetrate the mold 100, and each have a conical shape, forming a vacuum at the lower sides of the holes 200, and then injecting the biocompatible polymer solution containing an appropriate amount of active ingredient by using the filling needles 350; (b) a secondary filling step of injecting the biocompatible polymer solution containing the excipient by using the filling needle 350; (c) a step of solidifying the biocompatible polymer solution; and (d) a step of attaching the pad to the upper portion of the mold 100 and detaching the pad from the mold 100.

As illustrated in FIG. 2, a second method according to the present invention sequentially fills the multiple holes 200 with an appropriate amount of the completely prepared solution having the biocompatible polymer and the main ingredient by using the stoppers and the fine filling needles 350 (S211 and S212). In the case of a material with high viscosity, the vacuum is simultaneously applied. After the holes are completely filled, the holes are filled with the solution containing the biocompatible polymer secondarily or tertiarily (S213), and the reason is that this process serves to push the main ingredient of the raw liquid so that the ingredient is positioned at the end of the needle, and the protruding portion at the upper portion is a portion to be attached to the pad (tape) (S214). In some instances, the tertiary filling applies cosmetics onto the upper portion of the mold 100 and pushes the cosmetics by using a roller 700, thereby drawing the needles at one time. The tertiary filling is completed, a thickness is made constant once more, and then the mold is moved to the chamber to solidify the solution. When the solidification is completed, the solidified material is separated from the mold 100 and attached onto the pad (tape). When the biocompatible polymer solution is solidified, the upper portion of the mold is attached to the pad, and the pad is attached in accordance with a degree to which the biocompatible polymer solution is solidified. This method may be applied to medicine, and there is an effect in that the main ingredient less affects the human body when this method is applied to the medicine.

As illustrated in FIG. 8 in detail, a predetermined amount of biocompatible polymer solution is injected by pressing the biocompatible polymer solution by the stoppers 300 at the upper side of the mold 100 according to the present invention while applying the vacuum at the lower side of the mold by using the vacuum pump 400, and whether all of the holes 200 are filled with the amount of injected solution and whether the biocompatible polymer solution is appropriately solidified after the biocompatible polymer solution is solidified may be checked by using the vision system. In this case, a temperature of the solution to be injected may be 10 to 65° C., and the temperature may vary depending on the nature, viscosity, and elasticity of the product. The second method may be used mainly for a solution having a large molecular weight or relatively high viscoelasticity and a coagulating material. A cross-linked biocompatible polymer, particularly, a biocompatible polymer having a high degree of cross-linking may be used as a polymer having high viscosity, and particularly, cross-linked hyaluronic acid or cross-linked hyaluronic acid with a degree of cross-linking of 3 to 10% may be used. The viscosity of the solution to which the present invention is applied may range from 50,000 CPs 1,000,000 CPs, and a range of the applied vacuum may be 100 to 450 torr, particularly, 106 to 402 torr, and more particularly, 250 to 350 torr. If the pressure is lower than 100 torr, there is a problem in that process costs are greatly increased due to a high vacuum, and if the pressure is higher than 450 torr, there is a problem in that an effect of the vacuum filling the holes with the solution is not exhibited. That is, it is possible to manufacture the microneedle having a constant shape by manufacturing the microneedle by using the method and the solution having the viscosity in the aforementioned range under the aforementioned pressure. In this case, 760 torr indicates the atmospheric pressure, and 0 torr indicates the absolute vacuum.

In addition, even in a case in which the needle has a small length, an appropriate amount of solution is applied onto the mold 100 having the multiple (several hundreds of) holes 200 which penetrates the mold 100 and each have a conical shape, and then the solution is suctioned from the lower side of the mold 100 by using the vacuum. In this case, for a vacuum suction time and the amount of suctioned solution, the time and a vacuum degree adjusting device may be used by applying a verified method so that the vacuum suction is completed at the moment when the solution forms at the end of the needle.

In addition, still another aspect of the present invention relates to a method of manufacturing a biocompatible polymer-based microneedle, the method including: (a) a primary filling step of positioning the pad at the lower side of the bottom of the mold 100 having the multiple holes 200, which are formed to be spaced apart from one another, penetrate the mold, and each have a conical shape to seal the lower side of the bottom of the mold, covering, by the vacuum stoppers, the upper sides of the holes 200, dripping the biocompatible polymer solution containing an appropriate amount of active ingredient in the vacuum state, releasing the vacuum, and then filling the holes with the biocompatible polymer solution; (b) a secondary filling step of injecting the biocompatible polymer solution containing the excipient by using the filling needles 350; (c) a step of solidifying the biocompatible polymer solution; and (d) a step of attaching the pad to the upper portion of the mold 100 and then detaching the pad from the mold 100.

This method is a method of removing air at a tip and changing a position with a liquid chemical in a case in which the mold 100 is fine such that a very fine needle is made.

As illustrated in FIG. 3, a third method according to the present invention sequentially fills the multiple hole 200 with an accurate amount of the completely prepared solution having the biocompatible polymer and the main ingredient by using the vacuum stoppers 310 and the fine filling needles 350 in the vacuum state through a vacuum pump valve 450 (S311 and S312). Simultaneously, the bottom of the mold 100 is sealed by using the pad made of silicone or rubber. The main ingredient solution is dropped into the holes 200, and the vacuum is released by a vacuum releasing valve 500, such that the air in the holes 200 is removed, and the holes 200 are filled with the solution containing the main ingredient. After the holes are completely filled, the holes are filled with the solution containing the biocompatible polymer secondarily or tertiarily (S313), and the reason is that this process serves to push the main ingredient of the raw liquid so that the main ingredient is positioned at the end of the needle, and the protruding portion at the upper portion is a portion to be attached to the pad (tape) (S314). In some instances, the tertiary filling applies cosmetics onto the upper portion of the mold 100 and pushes the cosmetics by using a roller 700, thereby drawing the needles at one time. After the tertiary filling is completed, a thickness is made constant once more, and then the mold is moved to the chamber to solidify the solution. When the solidification is completed, the solution is separated from the mold 100 and attached onto the pad (tape).

As illustrated in FIG. 9, the lower portion of the mold 100 according to the present invention is covered by the pad such as a silicone pad or a rubber pad, the vacuum is applied to the upper portion of the mold 100 by using the vacuum stoppers 310, the holes are filled with a predetermined amount of solution in the vacuum state, and the vacuum is released by the vacuum releasing valve 500 after the holes are completely filled, such that the holes 200 are filled with the solution. In this case, the pad at the lower side is removed, and whether all of the holes 200 are filled with the amount of injected solution is checked by using the vision system. Another sealing plate may be used for the lower portion of the mold. Here, a temperature of the solution to be injected may be 10 to 65° C. The temperature may vary depending on the nature, viscosity, and elasticity of the product.

The process of the method of manufacturing the biocompatible polymer-based microneedle according to the present invention may be performed as follows.

As illustrated in FIG. 4, the upper portion of the mold 100 is filled with a predetermined amount of the completely prepared biocompatible polymer solution (S411). The biocompatible polymer solution with a constant thickness is applied onto the mold 100 by using the roller 700 (S0412, primary filling state). The biocompatible polymer solution is suctioned from the bottom of the mold 100 by using the vacuum pump and a vacuum frame. In this case, the suction time and the amount of suctioned solution are determined in accordance with the solution. The mold is filled with a predetermined amount of biocompatible polymer solution once more (S413). The thickness is made constant once more by the roller 700 (S414, secondary filling state), and the mold is moved to the chamber to solidify the solution. When the solidification is completed, the solution is separated from the mold 100 and attached onto the pad (tape).

Therefore, yet another aspect of the present invention relates to a method of manufacturing a biocompatible polymer-based microneedle, the method including: (a) a step of applying, by using the roller 700, an appropriate amount of biocompatible polymer solution onto the mold 100 having the multiple holes 200 which are formed to be spaced apart from one another, penetrate the mold 100, and each have a conical shape, and injecting the biocompatible polymer solution by connecting the lower sides of the holes 200 of the mold 100 to the vacuum pump; (b) a step of repeating step (a) one to ten times; (c) a step of solidifying the biocompatible polymer solution; and (d) a step of attaching the pad to the upper portion of the mold 100 and then detaching the pad from the mold 100.

The method according to the present invention is a method in which the stoppers 300 cover the upper sides of the multiple conical holes 200 formed to be spaced apart from one another in the mold 100 and then press the solution, a method in which the stoppers cover the upper sides of the holes 200 of the mold 100 and the lower sides of the holes 200 are connected to the vacuum pump, or a method in which the pad is positioned at the lower portion of the bottom of the mold 100 to seal the lower portion of the bottom of the mold 100, the vacuum stoppers cover the upper sides of the holes 200, the upper sides of the holes 200 are connected to the vacuum pump, the biocompatible polymer solution containing an appropriate amount of active ingredient is dripped in the vacuum state, and the vacuum is released, such that a predetermined amount of solution is injected, in which the primary filling injects the solution containing the main ingredient first, the secondary filling applies the excipient to accurately move the main ingredient to the end of the needle, and finally, the biocompatible polymer solution having a larger molecular weight is sufficiently applied onto the mold or an underlying layer capable of being attached to the pad is made.

Design is performed such that an accurate amount of biocompatible polymer solution is injected so that the main ingredient in the biocompatible polymer solution is accurately positioned at the end of the needle. The method of the present invention may be applied to medicine, particularly, biological medicine.

The number of times of application is determined depending on the amount of polymeric solution which is applied once, and the number of times of application may also vary depending on viscosity of the solution. The higher the viscosity, the larger the number of times, and the number of times may be 1 to 10.

The mold 100, which is filled with the solution injected and solidified to manufacture the biocompatible polymer-based microneedle, is tested by the vision system (medicine) or with the naked eye, such that whether the mold 100 is appropriately filled is checked, and then the mold is moved to the chamber to solidify the solution. When the solution is appropriately solidified, the pad is attached to the mold 100 and simultaneously detached from the mold 100. In this case, other methods may be used in accordance with products. Whether the pad is completely attached is checked. Additional solidification or drying is performed so that the needle is not contaminated and strength and hardness of the needle do not deteriorate for an effective period of time. In the case of a very sensitive product, freeze-drying is performed to adjust the amount of moisture to 3% or less. The needle is primarily packaged by blistering or thermal forming so that the needle is not lost, and the needle is secondarily packaged by using an aluminum pouch and a dehumidifying agent. The needle is finally packaged by using a carton box above the needle, and the package is completed by imparting a manufacturing number and a manufacturing date.

According to the present invention, the microneedle is manufactured by the aforementioned manufacturing method by using a biocompatible polymer, particularly, sodium hyaluronic acid, such that the microneedle delivers a main substance required for cosmetics and medicines to an appropriate position.

The microneedle of the present invention applied to cosmetics is a short needle having a size suitable to apply the cosmetics to the extent that the cosmetics stimulate skin, and the microneedle may exhibit an improvement on wrinkles, whitening, skin activation, and other functionality. In particular, in the case in which the cross-linked hyaluronic acid is used, the effect continues for a significant period of time, and other functional substances are slowly released in a sustained release manner, such that there is an advantage in that the cross-linked hyaluronic acid acts while remaining for a long period of time.

In addition, in the case in which the microneedle is used for a medicine purpose, the phobia to needles may be avoided, the microneedle is simply carried, and anyone may easily inject medicine. In particular, in a case of a patient who gets an injection every day, stiff and deformed muscle as well as the phobia to needles may be caused, but the microneedle may solve the inconvenience to the patient who needs to go to the hospital for prescriptions and treatments. Therefore, a patient may give himself/herself a treatment (injection) at the right time regardless of time and place. In addition, it can be said that there is an effect in that a shock caused by a rapid injection may be minimized. Regarding a difference from a microneedle product in the related art, since the end of the needle is sharp at a level of 25 to 30%, the needle is easily inserted deep into skin, such that the needle sufficiently exhibits its own effect, and since the needle is relatively thin, a patient feels less the needle when the needle is inserted into the skin. In addition, the product in the related art cannot administer an accurate amount of main ingredient of medicine into a desired site, but the microneedle according to the present invention may administer medicine significantly accurately to a necessary site.

In the present invention, the biocompatible polymer may be, but not limited to, a soluble substance derived from a body which is at least one of hyaluronic acid (HA), gelatin, chitosan, collagen, alginic acid, pectin, carrageenan, chondroitin (sulfate), dextran (sulfate), polylysine, carboxymethylchitin, fibrin, agarose, pullulan, and cellulose; or a biocompatible polymer or a cross-linked biocompatible polymer which is at least one of polyvinylpyrrolidone (PVP), polyethyleneglycol (PEG), polyvinylalcohol (PVA), hydroxypropylcellulose (HPC), hydroxyethylcellulose (HEC), hydroxypropylmethylcellulose (HPMC), carboxymethylcellulose sodium, polyalcohol, arabic gum, alginate, cyclodextrin, dextrin, glucose, fructose, starch, trehalose, glucose, maltose, lactose, lactulose, fructose, turanose, melitose, melezitose, dextran, sorbitol, xylitol, palatinit, polylactic acid, polyglycolic acid, polyethylene oxide, polyacrylic acid, polyacrylic amide, polymethacrylic acid, and polymaleic acid, preferably, hyaluronic acid or cross-linked hyaluronic acid, gelatin, or cross-linked gelatin. A molecular weight of the biocompatible polymer is within a range of 10,000 to 4,000,000 Da.

A cross-linking agent used to cross-link the cross-linked biocompatible polymer may be 1,2,7,8-diepoxyoctane, divinyl sulfone (DVS), glutaraldehyde, 1,4-butanediol diglycidyl ether (BDDE), vinyl sulfide, or polyethylene oxide. Preferably, BDDE is used, but the present invention is not limited thereto.

A process of manufacturing the mold 100 according to the present invention as illustrated in FIG. 5 is not particularly limited, and the mold 100 may be manufactured by a method in the related art.

The conical penetrating holes 200 are formed in all iron plates including stainless steel or all available plastic materials such as polycarbonate or polypropylene by using a drill or a laser.

FIG. 6A illustrates a cross section of a mold 110 for a cosmetic purpose, and FIG. 6B illustrates a cross section of a mold 120 for a medicine purpose.

For impregnation of cosmetics, a length (depth) of a hole in a plate or a die-casting hole is 50 to 270 µm, a diameter of a large hole is 30 to 80 µm, a diameter of a small hole is 10 to 50 µm, and the small hole is adjusted in accordance with the large hole. Nutrients and active ingredients need to be supplied to a site immediately before a horny layer, a transparent layer, an isolation layer, a stratum spinosum, and an underlying layer, and as a result, the microneedle needs to be mainly designed to be applied to epidermal tissue.

A length of the microneedle for impregnation of medicine is 600 μm or less, and the microneedle needs to be designed such that the active ingredient is supplied from a lower end of the underlying layer except for the horny layer, the transparent layer, the isolation layer, and the stratum spinosum, and as a result, the microneedle needs to be designed such that the active ingredient accurately exists to the end of the needle from a point spaced, by about 50 μm (0.1 mm), apart from an underlying portion of the microneedle and the active ingredient may be measured. This configuration may vary depending on an ingredient of medicine and a degree of obesity of a patient. At a portion of the conical hole where the active ingredient exists, similar to the microneedle for a cosmetic purpose, a diameter of a large hole is 30 to 80 μm, and a diameter of the end of the microneedle, which comes into contact with the skin, may be adjusted within a range of 10 to 70 μm. The mold 100 has various shapes modified as necessary.

The main feature of the present invention is that in the case of the microneedle used for a medicine purpose, the microneedle needs to be designed such that all active ingredients may be injected. In this production system, all of the holes 200 are related directly to an injection amount of active ingredients, such that a sufficient number of holes are manufactured to include a total amount of main ingredients, sub-ingredients, and solvents so that the holes are filled with a necessary amount of main ingredients, sub-ingredients, and solvents and the main ingredients and the sub-ingredients are solidified. In the case of the microneedle for a cosmetic purpose, since the active ingredient is applied to an overall length of the needle and skin care is important, the cosmetic needs to have a thickness equal to or smaller than a thickness of the needle, and the thickness and the length need to be maintained so that the time it takes for the cosmetic to melt is limited to at most 30 minutes so that there is no inconvenience within a zone of life.

In the case of the microneedle for a medicine purpose, the microneedle is required not to exceeds the aforementioned dimension so that the microneedle is free from the phobia to needles in a situation in which the maximum advantage of the microneedle is to overcome the phobia to needles, the overall time it takes for the medicine to melt needs to be adjusted to at most 30 minutes to several hours, and the microneedle needs to be designed so that a hypodermic injection effect occurs in stratum spinosum, conium, and subcutaneous tissue.

A melting speed may vary depending on mixtures or proportions of low molecular components and high molecular components of the hyaluronic acid and a cross-linking method.

The length and the thickness of the microneedle needs to be determined in sufficient consideration of a shrinking phenomenon that occurs during the solidification.

In the case of the microneedle according to the present invention for a biological or medicine product, a necessary amount of solution is injected first by using the stoppers 300. Then, the amount of solution, which is to be attached to the patch, is additionally injected. A method according to the present invention is as follows.

(1) As a method of filling the holes doubly, the solution containing the active ingredient is applied first, and then the portion to be attached to the patch is applied secondarily or multiple times. This method applies an accurate amount of solution such that the active ingredient is positioned at the end of the needle and the remaining solution is maintained in a sub-form, or the method additionally applies the solution to be attached to the pad in consideration of the amount of solution that shrinks.

(2) As a tube-in-tube filling method, the active ingredient enters a center.

In this case, the mold may be used regardless of whether the holes 200 penetrate the mold. FIG. 10 illustrates the manufactured biocompatible polymer-based microneedle.

In the case in which the active ingredient is a cosmetically active ingredient, a length of the microneedle from the lower end of the underlying layer to the end of the needle is 50 to 270 μm, a diameter of the lower end of the underlying layer is 30 to 80 μm, a diameter of the end of the needle is 10 to 50 μm, and a cosmetically active ingredient, an excipient, and a patch attachment portion including a biocompatible polymer matrix may be sequentially applied from the end of the needle.

In addition, in the case in which the active ingredient is medicine, a length from the lower end of the underlying layer to the end of the needle is 600 μm or less, a diameter of the lower end of the underlying layer is 100 to 400 μm, a diameter of the end of the needle is 10 to 70 μm, and a pharmaceutically active ingredient, an excipient, and a patch attachment portion including a biocompatible polymer matrix may be sequentially applied from the end of the needle.

With this structure, the active ingredient may be injected to a maximally perfectly accurate position without pain.

After the filling, the microneedle according to the present invention may be solidified by blowing air at a temperature of 5 to 30° C. or blowing air at a temperature of 80° C. or more, or by rapid freeze drying.

A hole is formed in a portion (attachment portion) of the patch or the pad, on which the microneedle is placed to facilitate the solidification, and the hole allows a user to have an air blowing effect so that the microneedle is prevented from being deformed.

Solidification methods include, but not limited to, a method of blowing air by adjusting a temperature to 5 to 30° C. for a biological product, a method of blowing air at a temperature of 80° C. or more to a general chemical product, particularly, a product having no heat sensitivity, a solidification method using a temperature of 65 to 90° C. and a method simultaneously using air blowing or a combination of these two methods, and a method of maintain a significantly low moisture content through rapid freeze drying.

The application range of the microneedle according to the present invention corresponds to all of a patch type filler, a patch type botox, remicade and a biosimilar thereof, Enbrel and a biosimilar thereof, Humira and a biosimilar thereof, small molecule protein, for example, a biological protein product with a low capacity such as insulin, human growth hormone, parathyroid hormone (PTH), granulocyte colony-stimulating factor (GCSF), interferon A'R, and follicle-stimulating hormone (FSH). In addition, the application range also includes vaccine, antibiotics with a low capacity, anti-cancer drug, and chemical products.

Therefore, another aspect of the present invention relates to a cross-linked hyaluronic acid-based microneedle in which a length from the lower end of the underlying layer to the end of the needle is 600 μm or less, a diameter of the lower end of the underlying layer is 100 to 400 μm, a diameter of the end of the needle is 10 to 70 μm, and a cross-linked hyaluronic acid matrix, which contains a pharmaceutically active ingredient and an excipient and has a degree of cross-linking of 1 to 10%, is sequentially applied from the end of the needle.

In addition, still another aspect of the present invention relates to a cross-linked hyaluronic acid-based microneedle in which a length from the lower end of the underlying layer to the end of the needle is 50 to 270 μm, a diameter of the lower end of the underlying layer is 30 to 80 μm, a diameter of the end of the needle is 10 to 50 μm, and a cross-linked hyaluronic acid matrix, which contains a cosmetically active ingredient and an excipient and have a degree of cross-linking of 1 to 10%, is sequentially applied from the end of the needle.

The cross-linked hyaluronic acid-based microneedle means a microneedle using cross-linked hyaluronic acid. The degree of cross-linking of the cross-linked hyaluronic acid may be 1 to 10%, preferably, 3 to 6%, and productivity is excellent within this range. A cross-linking agent used to cross-link the cross-linked hyaluronic acid may be 1,2,7,8-diepoxyoctane, divinyl sulfone (DVS), glutaraldehyde, 1,4-butanediol diglycidyl ether (BDDE), vinyl sulfide, or polyethylene oxide. Particularly, BDDE is used, but the present invention is not limited thereto.

Hereinafter, the present invention will be described in more detail through Examples. The Examples are provided only to describe the present invention and may be selectively changed in accordance with substances or chemicals, and it will be apparent to those skilled in the art that the scope of the present invention is not limited to the Examples.

EXAMPLES

Example 1: Manufacture of Microneedle Using Hyaluronic Acid

Hyaluronic acid and a main ingredient (insulin) was inputted into a tank after measuring the hyaluronic acid and the main ingredient. The hyaluronic acid and the main ingredient were mixed until the entire solution became homogeneous such that the preparation was completed, and then the solution was inputted into a filling tank.

In accordance with the processes illustrated in FIGS. 1 to 3, the multiple holes were filled with the cross-linked hyaluronic acid solution by using the stoppers and the fine filling needles at the upper side of the mold. After the holes were completely filled, the cross-linked hyaluronic acid solution containing the excipient was applied secondarily, and the cross-linked hyaluronic acid was applied tertiarily. The filled mold was tested by the vision system (medicine) or with the naked eye, such that whether the mold was appropriate was checked, and the mold was moved to the chamber to solidify the polymer. When the polymer was appropriately solidified, the pad was attached to the mold and simultaneously detached from the mold, and whether the polymer was perfectly attached to the pad was checked. Additional solidification or drying was performed.

The needle was primarily packaged by blistering or thermal forming so that the needle was not lost, and the needle was secondarily packaged by using an aluminum pouch and a dehumidifying agent. The needle was finally packaged by using a carton box above the needle, and the package was completed by imparting a manufacturing number and a manufacturing date.

Example 2: Manufacture of Microneedle for Medicine Purpose by Using Cross-Linked Hyaluronic Acid Hyaluronic acid was cross-linked by mixing and incubating the hyaluronic acid and a cross-linking agent In this case, the hyaluronic acid cross-linked by 3 to 5% was used. The process is performed aseptically. Patch type cross-linked hyaluronic acid (HA) (a substitute of a filler) and a main ingredient were inputted into a tank after measuring the patch type cross-linked hyaluronic acid and the main ingredient. The hyaluronic acid and the main ingredient were mixed until the entire solution became homogeneous such that the preparation was completed, and then the solution was transferred into a filling tank.

In accordance with the processes illustrated in FIGS. 1 to 3, the multiple holes were filled with the cross-linked hyaluronic acid solution by using the stoppers and the fine filling needles at the upper side of the mold. After the holes were completely filled, the cross-linked hyaluronic acid solution containing the excipient was applied secondarily, and the cross-linked hyaluronic acid was applied tertiarily. The filled mold was tested by the vision system (medicine) or with the naked eye, such that whether the mold was appropriate was checked, and the mold was moved to the chamber to solidify the polymer. When the polymer was appropriately solidified, the pad was attached to the mold and simultaneously detached from the mold, and whether the polymer was perfectly attached to the pad was checked. Additional solidification or drying was performed.

The needle was primarily packaged by blistering or thermal forming so that the needle was not lost, and the needle was secondarily packaged by using an aluminum pouch and a dehumidifying agent. The needle was finally packaged by using a carton box above the needle, and the package was completed by imparting a manufacturing number and a manufacturing date.

FIG. 11 illustrates the cross-linked hyaluronic acid-based microneedle for a medicine purpose which was manufactured according to the exemplary embodiment of the present invention and captured by a microscope (magnification of ×60).

As illustrated in FIG. 11, it could be ascertained that in the cross-linked hyaluronic acid-based microneedle for a medicine purpose according to Example 2, a length from the lower end of the underlying layer to the end of the needle was 600 μm or less, a diameter of the lower end of the underlying layer was 100 to 400 μm, a diameter of the end of the needle was 10 to 70 μm, a pharmaceutically active ingredient, an excipient, and a patch attachment portions including a cross-linked hyaluronic acid matrix was sequentially applied from the end of the needle, the microneedle has a diameter, hardness and a length that may penetrate into skin, and the microneedle, which had a perfect shape, might be simply manufactured.

Example 3: Manufacture of Microneedle for Cosmetic Purpose

Hyaluronic acid was cross-linked by mixing and incubating the hyaluronic acid and a cross-linking agent. In this case, the hyaluronic acid cross-linked by 3 to 5% was used. The process is performed aseptically. Patch type cross-linked hyaluronic acid (HA) (a substitute of a filler) and a cosmetically active ingredient (Group A: sterilized adenosine, copper peptide, hexapeptide, EGF, glyceryl glucoside (GG) propolis, dipotassium glycyrrhizate, glycyrrhiza extract, and allantoin; and Group B: sterilized adenosine, niacinamide, vitamin E acetate, vitamin C, propolis, dipotassium glycyrrhizate, glycyrrhiza extract, allantoin, and green tea extract) were inputted into a tank after measuring the patch type cross-linked hyaluronic acid and the cosmetically active ingredient. The hyaluronic acid and the main ingredient were mixed until the entire solution became homogeneous such that the preparation was completed, and then the solution was inputted into a filling tank.

A predetermined amount of the cross-linked hyaluronic acid solution, which was completely prepared according to the process illustrated in FIG. 4, was applied onto the mold, and the cross-linked hyaluronic acid solution with a constant thickness was applied onto the mold by using the roller. The biocompatible polymer solution was suctioned from the bottom of the mold by using the vacuum pump and a vacuum frame. A predetermined amount of biocompatible polymer solution was applied once more, the thickness was made constant by the roller once more, and the mold was moved to the chamber for solidification. When the polymer was appropriately solidified, the pad was attached to the mold and simultaneously detached from the mold, and whether the polymer was perfectly attached to the pad was checked. Additional solidification or drying was performed.

The needle was primarily packaged by blistering or thermal forming so that the needle was not lost, and the needle was secondarily packaged by using an aluminum pouch and a dehumidifying agent. The needle was finally packaged by using a carton box above the needle, and the package was completed by imparting a manufacturing number and a manufacturing date.

FIGS. 12A-12D illustrate the cross-linked hyaluronic acid-based microneedle for a cosmetic purpose which was manufactured according to the exemplary embodiment of the present invention and captured by a microscope (magnification of ×60).

FIGS. 12A-12D are photomicrographs (magnification of ×60) obtained by capturing an elevational view (FIG. 12A) and a side view (FIG. 12B) of a low-concentration cross-linked hyaluronic acid-based microneedle manufactured according to Example 2, and photomicrographs (magnification of ×60) obtained by capturing an elevational view (FIG. 12C) and a side view (FIG. 12D) of a high-concentration cross-linked hyaluronic acid-based microneedle.

Comparative Examples 1 to 3: Microneedle for Cosmetic Purpose in Related Art

Images of commercially available microneedles for a cosmetic purpose from Companies A, B, and C were captured by a microscope and compared with that of Example 2 of the present invention.

FIGS. 13A and 13B are photomicrographs (magnification of ×60) obtained by capturing an elevational view (FIG. 13A) and a side view (FIG. 13B) of a commercially available microneedle from Company A, FIG. 14 is photomicrographs (magnification of ×60) obtained by capturing an elevational view (left) and a side view (right) of a commercially available microneedle from Company B, and FIGS. 15A-15E are photomicrographs obtained by capturing an elevational view (FIG. 15A), an elevational zoom-in view (FIG. 15B), a side view (FIG. 15C), an edge (FIG. 15D), and an attachment portion (FIG. 15E) of a commercially available microneedle from Company C.

As illustrated in FIGS. 12A-12D, it could be ascertained that the microneedle for a cosmetic purpose according to Example 2 of the present invention had a diameter, hardness, and a length that may sufficiently stimulate the skin, and the microneedle, which has a perfect shape, might be simply manufactured.

In contrast, the microneedle in the related art never had a shape of the microneedle and did not have a diameter, hardness, and a length that may be used for a cosmetic purpose.

INDUSTRIAL APPLICABILITY

The end of the needle of the biocompatible polymer-based microneedle manufactured according to the present invention is sharp at a level of 25 to 30% in comparison with that of the needle in the related art, such that the needle is easily inserted into skin and penetrate deep into the skin, and since the needle is thinner than the microneedle in the related art, a patient feels less the microneedle when the microneedle is inserted into the skin, and the microneedle may accurately inject medicine to a target site without causing a degeneration or loss of the medicine. The microneedle in the related art cannot be manufactured aseptically, and it is difficult to accurately position the main ingredient only at a necessary site, and as a result, there is a limitation in using the microneedle in the related art for a medicine purpose.

In addition, it is possible to solve the problem of a phobia to needles and stiff and deformed muscle caused by the microneedle in the related art, and to solve the inconvenience to the patient who needs to go to the hospital for prescriptions and treatments, such that the patient may give himself/herself a treatment (injection) at the right time regardless of time and place, there is an effect in that a shock caused by a rapid injection may be minimized, and the microneedle is more simply manufactured in a short time in comparison with a method of manufacturing the microneedle in the related art.

Although the specific part of the present invention has been described in detail, it will be obvious to those skilled in the art that such a specific description is just a preferred embodiment and the scope of the present invention is not limited thereby. Accordingly, the substantial scope of the present invention will be defined by the appended claims and equivalents thereof.

The invention claimed is:

1. A method of manufacturing a biocompatible polymer-based microneedle, the method comprising:
    (a) a primary filling step of covering upper sides of a plurality of conical shaped holes that penetrate a mold using stoppers, and injecting a first biocompatible polymer solution containing an appropriate amount of active ingredient into the holes using filling needles coupled to the stoppers;
    (b) a secondary filling step of injecting a second biocompatible polymer solution containing an excipient into the holes by using the filling needles;
    (c) a step of solidifying the first biocompatible polymer solution and the second biocompatible polymer solution; and
    (d) a step of attaching a tape to an upper portion of the mold after the solidifying step (c) is completed and then detaching the tape from the mold.

2. The method according to claim 1, wherein a vacuum is formed at lower sides of the holes while injecting the first biocompatible polymer solution in the primary filling step (a).

3. A method of manufacturing a biocompatible polymer-based microneedle, the method comprising:
    (a) a primary filling step of sealing a lower side of a mold penetrated by a plurality of conical shaped holes by positioning a pad at the lower side of the bottom of the mold, covering upper sides of the holes with vacuum stoppers, applying a vacuum to the holes, dripping a first biocompatible polymer solution containing an active ingredient into the holes using filling needles coupled to the vacuum stoppers, and releasing the vacuum to fill bottom portions of the holes with the first biocompatible polymer solution;

(b) a secondary filling step of injecting a second biocompatible polymer solution containing an excipient into the holes by using the filling needles;

(c) a step of solidifying the first biocompatible polymer solution and the second biocompatible polymer solution; and (d) a step of attaching a tape to an upper portion of the mold after the solidifying step (c) is completed and then detaching the tape from the mold.

4. The method according to claim 1 or 3, further comprising:
a tertiary filling step of injecting a third biocompatible polymer solution having a larger molecular weight than the first biocompatible polymer solution and the second biocompatible polymer solution into the holes by using the filling needles after secondary filling step (b).

5. The method according to claim 3, wherein when the vacuum is released, air in the holes is removed, such that the holes are filled with the first biocompatible polymer solution.

6. The method according to claim 1 or 3, further comprising:
a step of checking whether all of the holes are filled with the first biocompatible polymer solution and the second biocompatible polymer solution and whether the first biocompatible polymer solution and the second biocompatible polymer solution are solidified by a vision system.

7. The method according to claim 1 or 3, further comprising:
a step of additionally solidifying or drying the first biocompatible polymer solution and the second biocompatible polymer solution after step (c).

8. The method according to claim 1 or 3, wherein the first and second biocompatible polymer solutions include one or more biocompatible polymer selected from a group consisting of hyaluronic acid (HA), gelatin, chitosan, collagen, alginic acid, pectin, carrageenan, chondroitin (sulfate), dextran (sulfate), polylysine, carboxymethylchitin, fibrin, agarose, pullulan, cellulose, polyvinylpyrrolidone (PVP), polyethyleneglycol (PEG), polyvinylalcohol (PVA), hydroxypropylcellulose (HPC), hydroxyethylcellulose (HEC), hydroxypropylmethylcellulose (HPMC), carboxymethylcellulose sodium, polyalcohol, arabic gum, alginate, cyclodextrin, dextrin, glucose, fructose, starch, trehalose, maltose, lactose, lactulose, fructose, turanose, melitose, melezitose, dextran, sorbitol, xylitol, palatinit, polylactic acid, polyglycolic acid, polyethylene oxide, polyacrylic acid, polyacrylic amide, polymethacrylic acid, and polymaleic acid.

9. The method according to claim 8, wherein the biocompatible polymer is hyaluronic acid.

10. The method according to claim 1 or 3, wherein the stopper is made of silicone or rubber.

11. The method according to claim 1 or 3, wherein the mold includes a material selected from a group consisting of stainless steel, iron, and plastic.

12. The method according to claim 1 or 3, wherein temperatures of the first biocompatible polymer solution and the second biocompatible polymer solution are 10 to 65° C.

13. The method according to claim 1 or 3, wherein the first biocompatible polymer solution and the second biocompatible polymer solution are solidified by blowing air at a temperature of 5 to 30° C. or blowing air at a temperature of 80° C. or more, or by rapid freeze drying.

14. The method according to claim 1 or 3, wherein the active ingredient is a cosmetically active ingredient, a length of the microneedle from a lower end of an underlying layer to an end of a needle is 50 to 270 μm, a diameter of the lower end of the underlying layer is 30 to 80 μm, a diameter of the end of the needle is 10 to 50 μm, and a cosmetically active ingredient, an excipient, and a patch attachment portion including a biocompatible polymer matrix is sequentially applied from the end of the needle.

15. The method according to claim 1 or 3, wherein the active ingredient is a pharmaceutically active ingredient, a length of the microneedle from a lower end of an underlying layer to an end of a needle is 600 μm or less, a diameter of the lower end of the underlying layer is 100 to 400 μm, a diameter of the end of the needle is 10 to 70 μm, and a pharmaceutically active ingredient, an excipient, and a patch attachment portion including a biocompatible polymer matrix is sequentially applied from the end of the needle.

\* \* \* \* \*